(12) United States Patent
Weaver et al.

(10) Patent No.: US 8,954,131 B2
(45) Date of Patent: Feb. 10, 2015

(54) MAGNETIC PARTICLE IMAGING (MPI) SYSTEM AND METHOD FOR USE OF IRON-BASED NANOPARTICLES IN IMAGING AND DIAGNOSIS

(75) Inventors: John B. Weaver, Hanover, NH (US); Jose R. Conejo-Garcia, East Thetford, VT (US); Steven N. Fiering, Orange, NH (US); Adam M. Rauwerdink, W. Lebanon, NH (US); Uciane K. Scarlett, Lebanon, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 700 days.

(21) Appl. No.: 12/912,570

(22) Filed: Oct. 26, 2010

(65) Prior Publication Data

US 2011/0098558 A1 Apr. 28, 2011

Related U.S. Application Data

(63) Continuation-in-part of application No. 12/141,844, filed on Jun. 18, 2008, now Pat. No. 7,994,786.

(60) Provisional application No. 60/974,105, filed on Sep. 21, 2007, provisional application No. 60/944,901, filed on Jun. 19, 2007.

(51) Int. Cl.
*A61B 5/055* (2006.01)
*B82Y 25/00* (2011.01)
(Continued)

(52) U.S. Cl.
CPC .............. *A61B 5/05* (2013.01); *A61B 5/0515* (2013.01); *B82Y 25/00* (2013.01); *G01R 33/4808* (2013.01); *G01R 33/5601* (2013.01); *A61B 5/055* (2013.01); *H01F 1/0045* (2013.01)
USPC .......................................... 600/420; 324/300

(58) Field of Classification Search
USPC .......... 324/300–322; 600/407–435, 437, 453, 600/12; 382/128–131; 424/9.6, 9.34, 9.321, 424/9.2, 9.322, 9.362, 9.3, 490; 435/7.2; 540/122, 139
See application file for complete search history.

(56) References Cited

U.S. PATENT DOCUMENTS 6,355,275 B1 * 3/2002 Klein ............................ 424/490
7,423,429 B2 * 9/2008 Hernandez Perez et al. . 324/309
(Continued)

FOREIGN PATENT DOCUMENTS

EP 2022508 A1 2/2009
WO WO2004091386 A2 10/2004
(Continued)

OTHER PUBLICATIONS

Anderson, et al., "Assessing Lead Time of Selected Ovarian Cancer Biomarkers: A Nested Case-Control Study", "JNCI", Jan. 6, 2010, pp. 26-38, vol. 102, No. 1, Publisher: Oxford University Press, Published in: US.
(Continued)

*Primary Examiner* — Melissa Koval
*Assistant Examiner* — Tiffany Fetzner
(74) *Attorney, Agent, or Firm* — Loginov & Associates, PLLC; William A. Loginov

(57) ABSTRACT

A method for diagnosing certain types of cancers provides a nanoparticle agent to be uptaken by cancer cells for diagnosis and treatment of certain cancers. A compound containing nanoparticles is directed toward a tumor site, and then a predetermined time period passes to allow the nanoparticles to be uptaken by the cancer cells. Imaging is then performed on the nanoparticles by an appropriate imaging device to determine the concentration of nanoparticles uptaken by the cancer cells. Finally, image data provided by the imaging device is analyzed to determine the concentration of nanoparticles and thereby determine whether a tumor is present. The nanoparticle agent can further be employed as a treatment of certain cancers. After the uptake of nanoparticles into the cells, a predetermined field applied to the nanoparticles for a sufficient period of time activates the magnetic cores of the nanoparticles to include hyperthermia-mediated destruction of the cancer cells.

20 Claims, 19 Drawing Sheets

(51) Int. Cl.
  *A61B 5/05* (2006.01)
  *G01R 33/48* (2006.01)
  *G01R 33/56* (2006.01)
  *H01F 1/00* (2006.01)

(56) References Cited

U.S. PATENT DOCUMENTS

| | | | |
|---|---|---|---|
| 7,662,362 B2* | 2/2010 | Kuppusamy et al. | 424/9.3 |
| 7,994,786 B2* | 8/2011 | Weaver et al. | 324/318 |
| 8,066,973 B2* | 11/2011 | Kuppusamy et al. | 424/9.3 |
| 8,454,511 B2* | 6/2013 | Milner et al. | 600/437 |
| 8,568,694 B2* | 10/2013 | Kuppusamy et al. | 424/9.3 |
| 8,569,482 B2* | 10/2013 | Kuppusamy et al. | 540/139 |
| 2003/0085703 A1 | 5/2003 | Gleich | |
| 2005/0203292 A1* | 9/2005 | Kuppusamy et al. | 540/122 |
| 2007/0041909 A1* | 2/2007 | Kupussamy et al. | 424/9.362 |
| 2008/0226562 A1* | 9/2008 | Groves et al. | 424/9.6 |
| 2009/0043198 A1* | 2/2009 | Milner et al. | 600/437 |
| 2009/0115415 A1* | 5/2009 | Weaver et al. | 324/309 |
| 2009/0196831 A1 | 8/2009 | Yang et al. | |
| 2010/0172843 A1* | 7/2010 | Kuppusamy et al. | 424/9.34 |
| 2010/0292564 A1* | 11/2010 | Cantillon Murphy | 600/411 |
| 2011/0014129 A1* | 1/2011 | Zabow et al. | 424/9.34 |
| 2011/0098558 A1* | 4/2011 | Weaver et al. | 600/420 |
| 2011/0221438 A1* | 9/2011 | Goodwill et al. | 324/301 |
| 2011/0273176 A1* | 11/2011 | Weaver et al. | 324/301 |
| 2012/0201760 A1* | 8/2012 | Tromsdorf et al. | 424/9.322 |
| 2012/0276011 A1* | 11/2012 | Kupussamy et al. | 424/9.2 |
| 2013/0245357 A1* | 9/2013 | Chauhan et al. | 600/12 |
| 2013/0331701 A1* | 12/2013 | Milner et al. | 600/453 |
| 2014/0186268 A1* | 7/2014 | Vasiljeva et al. | 424/9.321 |

FOREIGN PATENT DOCUMENTS

| | | |
|---|---|---|
| WO | WO2006035359 A2 | 4/2006 |
| WO | WO2006122278 A2 | 11/2006 |
| WO | WO2006128167 A2 | 11/2006 |

OTHER PUBLICATIONS

Weaver, et al, "Imaging Magnetic Nanoparticles Using the Signal's Frequency Spectrum", Mar. 12, 2008, p. 8, vol. 6916, No. 35, Publisher: Dartmouth Hitchcock Medical Center Department of Radiology, Published in: Lebanon, NH.

Dahnke et al, "Limits of Detection of SPIO at 3.0T Using T2 Relaxometry", Jun. 17, 2004, pp. 1-14, vol. 6916, Publisher: Philips Research Laboratories, Technical Systems, Published in: Hamburg, Germany.

Kaiser, et al, "Magnetic Properties of Stable Dispersions of Subdomain Magnetite Particles", Mar. 1970, p. 9 vol. 41, No. 1-13, Publisher: Journal of Applied Physics, Published in: Lowell, MA.

Day, Charles, "Novel Medical Imaging Method Shows Promise", Sep. 2005, pp. 21-22, Publisher: Physics Today, Published in: US.

Cubillos-Ruiz, et al., "Polyethylenimine-Based siRNA Nanocomplexes Reprogram Tumor-Associated Dendritic Cells via TLR5 to Elicit Therapeutic ANT", "The Journal of Clinical Investigation", Aug. 2009, pp. 2231-2244, vol. 119, No. 8, Published in: US.

Gleich, et al, "Tomographic Imaging Using the Nonlinear Response of Magnetic Particles", Jun. 2005, pp. 1214-1217, vol. 435, No. 30, Publisher: Nature Publishing Group, Published in: Hamburg, Germany.

Conejo-Garcia, et al., "Tumor-Infiltrating Dendritic Cell Precursors Recruited by a B-Defensin Contribute to Vasculogenesis Under the Influence ", "Nature Medicine", Sep. 2004, pp. 950-958, vol. 10, No. 9, Published in: US.

John B. Weaver, et al., "Frequency Distribution of the Nanoparticle Magnetization in the Presence of a Static as Well as a Harmonic Magnetic Field", "Medical Physics", 5/00/2008, pp. 1988-1994, vol. 35, No. 5, Publisher: Am. Assoc. Phys. Med, Published in: US.

* cited by examiner

MAGNETIC PARTICLE IMAGING (MPI) SYSTEM AND METHOD FOR USE OF IRON-BASED NANOPARTICLES IN IMAGING AND DIAGNOSIS

RELATED APPLICATIONS

This application is a continuation-in-part of copending U.S. application Ser. No. 12/141,844, filed Jun. 18, 2008, entitled SYSTEM AND METHOD FOR USE OF NANOPARTICLES IN IMAGING AND TEMPERATURE MEASUREMENT, the entire disclosure of which is herein incorporated by reference, which claims the benefit of U.S. Provisional Application Ser. No. 60/944,901, filed Jun. 19, 2007, entitled SYSTEM AND METHOD FOR IMPROVED NANOPARTICLE LOCALIZATION AND IMAGING, the entire disclosure of which is herein incorporated by reference, and U.S. Provisional Application Ser. No. 60/974,105, filed Sep. 21, 2007, entitled SYSTEM AND METHOD FOR MEASURING TEMPERATURE USING THE SPECTRAL DISTRIBUTION OF MAGNETIC PARTICLE IMAGING SIGNALS, the entire disclosure of which is herein incorporated by reference.

STATEMENT REGARDING FEDERALLY SPONSORED RESEARCH OR DEVELOPMENT

This invention was made with U.S. government support under Grant Numbers R01CA124515, R21CA132026 and F31CA134188, awarded by the Norris Cotton Cancer Center. The government may have certain rights in this invention.

FIELD OF THE INVENTION

This invention relates to non-invasive imaging of magnetic particles, and more particularly to Magnetic Particle Imaging (MPI), and to using magnetic particles as biomarkers for measuring particle temperature and binding characteristics of infused magnetic particles.

BACKGROUND OF THE INVENTION

The localization and imaging of magnetic particles and particularly nanoparticles (e.g. discrete particulate structures sized in the nanometer range) is becoming increasingly important for developing new diagnostic methods. Magnetic particles (e.g. iron oxide or iron particles having a magnetic characteristic) have recently been employed in several forms of imaging including MRI (See: H. Dahnke and T. Schaeffter: *Limits of Detection of SPIO at 3.0 T Using T2 Relaxometry*, Magnetic Resonance in Medicine 53:1202-1206 (2005). Recently, a relatively new method termed "Magnetic Particle Imaging" or MPI. MPI was introduced in a paper by B. Gleich and J. Weizenecker entitled *Tomographic Imaging Using the Nonlinear Response of Magnetic Particles*, Nature Vol. 435 (30):1214-9 Jun. 2005. Currently, this new technique (MPI) has received a good deal of attention in the wider press because of the promise of the method. See: C. Day, *Novel Medical Imaging Method Shows Promise, Physics Today*, Sep. 21-22, 2005. The teachings of each of the above three articles/papers being expressly incorporated herein by reference.

Thus, magnetic particles are becoming important in a wide variety of endeavors and applications. In medical applications, such magnetic particles are being used to identify pathology as well as to treat pathology like cancer and heart disease. In general, magnetic substances are relatively easy to detect using various detection and imaging technologies. A further discussion of the use of MPI, in the imaging of human bodily structures is disclosed in published U.S. Patent Application No. 2003/0085703, entitled METHOD OF DETERMINING THE SPATIAL DISTRIBUTION OF MAGNETIC PARTICLES by Bernhard Gleich, the teachings of which are expressly incorporated herein by reference. Reference will now be made to FIGS. 1 and 2, which illustrate a basic implementation of an MPI system in accordance with Gleich.

The MPI system detects particles in the field-free point 210 (FIG. 2 below) where there is very little static field. Those particles in the field free point produce signal at the harmonics, most strongly at the third harmonic.

As shown in FIG. 1, a plurality 100a, 100b of coil pairs are arranged above (100a) and beneath (100b) a patient (or other subject to be examined) 110 positioned on a table top, which is substantially non-magnetic. As described further below, the patient has been infused with magnetic nanoparticles. These particles can be formed with a variety of substances and in a range of sizes. In one example, the particles each comprise a spherical substrate, for example, of glass which is covered with a soft magnetic layer having a thickness of, for example, approximately 5 nm. This layer can consist, for example, of an iron nickel alloy (for example, permalloy). This soft magnetic layer may be covered, for example, with a further covering layer, which protects the particle against acids and other bodily fluids and/or environmental agents.

The range of these coil pairs defines the examination zone. The first coil pair includes the two identically constructed windings 102a and 102b, which are arranged coaxially above and beneath the patient or sample and conduct equally large but oppositely directed sinusoidal currents (indicated by oppositely arranged X's and dots). The gradient magnetic field thus generated can be represented by the field lines 200 shown in FIG. 2. In the direction of the (perpendicular) axis of the coil pair it has a substantially constant gradient and in a point 202 on this axis (dashed line 210) it reaches the value zero. Starting from this field-free point, the strength of the magnetic field increases in all three spatial directions as a function of the distance from this point. In a zone 210 which is denoted by a dashed circle (the first sub-zone) around the field-free point the field strength is so low that the magnetization of magnetic particles present therein is not saturated, whereas the magnetization is in a state of saturation outside the zone 210. In the zone remaining outside the zone 210 (the second sub-zone 220) the magnetization of the particles is in the saturated state.

The strength of the magnetic field required for the saturation of the magnetization of particles is dependent on their diameter and composition. Smaller particle require a larger magnetic field to saturate them than larger particles. When a coating of a material having a lower saturation magnetization is chosen, lower field values are enabled. The size of the zone 301 determines the spatial resolution of the system, and is partly dependent on the strength of the gradient of the gradient magnetic field and also on the strength of the magnetic field required for saturation. By way of example, for a 100-micron diameter and a gradient of 0.2 T/m of the magnetic field, the zone 210 (in which the magnetization of the particles is not saturated) defines a size of approximately 1 mm.

In order to appropriately image structures within the patient or other subject 100 under examination, the system must extract information concerning the spatial concentration of the magnetic particles within the subject 100. As such, a plurality of coil winding pairs is arranged above and beneath the subject 100 and/or the table top 112.

When a further magnetic field is superimposed on the gradient magnetic field in the examination zone, the zone 210 is shifted in the direction of this additional magnetic field, the extent of the shift being greater as the strength of the magnetic field is greater. When the superimposed magnetic field is variable in time, the position of the zone 210 changes accordingly in time and in space.

In order to generate such temporally variable magnetic fields for any arbitrary direction in space, three further coil winding pairs 104a and 104b, 106a and 106b, and 108a and 108b are provided coaxially with the first winding pair 102a, 102b. The coil winding pair 104a, 104b generates a magnetic field which extends in the direction of the coil axis (dashed line 130) of the coil winding pair 102a, 102b (aligned vertically in this example). To this end, the two windings 104a, 104b are supplied with equal currents which also flow in the same direction as adjacent windings 102a, 102b. The effect of coil winding pair 104a, 104b can also be achieved by superimposing currents flowing in the same direction on the oppositely directed equal currents in the coil winding pair 102a, 102b so that the current in one coil pair decreases while it increases in the other coil winding pair. However, it may be advantageous when the temporally constant gradient magnetic field and the temporally variable vertical magnetic field are generated by separate coil pairs.

In order to generate magnetic fields which extend horizontally in space in the longitudinal direction of the patient/subject 100, and also in a direction perpendicular thereto (e.g. generally parallel to the axis 130), there are provided two further coaxial coil winding pairs 106a and 106b, and 108a and 108b. In this example the coil winding pairs 106a, 106b and 108a, 108b are not of a Helmholz-type—while the coil winding pairs 102a, 102b and 104a, 104b can be of a Helmholz-type. To employ Helmholz-type coil winding pairs to generate horizontal fields would require them to be arranged along the sides of the examination zone—for example, windings each respectively arranged to the left and to the right of the examination zone and in front of and behind the examination zone. This arrangement may be impractical, as it impeded access to the examination area.

Thus, as shown, the windings 106a, 106b and 108a, 108b of the coil pairs are arranged coaxially above and beneath the examination zone, and hence they employ a winding configuration different than that of the coil winding pair 104a, 104b. Note that coils of this configuration are known and available in connection with magnetic resonance apparatus with an open magnet (e.g. open MRI) in which an RF coil pair is arranged above and beneath the examination zone so as to generate a horizontal, temporally variable magnetic field.

FIG. 1 also shows a further pickup/sensing coil(s) 150 which provides for the detection of signals generated in the examination zone. In principle any of the field-generating coil winding pairs 102a and 102b, 104a and 104b, 106a and 106b, and/or 108a and 108b can be used for this purpose. However, the use of a separate receiving coil offers advantages. A more attractive signal-to-noise ratio is obtained (notably when a plurality of receiving coils is used) and the sensing coil(s) 150 can be arranged and switched in such a manner that it is decoupled from the other coils.

In operation, the coil winding pairs 104a and 104b, 106a and 106b, and 108a and 108b receive their currents from current amplifiers 170. The variation in time of the currents $I_x$, $I_y$, and $I_z$ which are amplified and produce the desired magnetic fields is imposed by a respective waveform generator 172. The waveform generators are controlled by a system control unit 174, which calculates the variation in time of the currents as required for the relevant examination method and loads this variation into the waveform generators. During the examination these signals are read from the waveform generators 172 and applied to the amplifiers 170, which generate the sinusoidal currents $I_x$, $I_y$, and $I_z$ required for the coil winding pairs 104a and 104b, 106a and 106b, and 108a and 108b on the basis thereof.

Generally, a non-linear relationship exists between the shift of the zone 210 from its position at the center of the gradient coil system 102a, 102b and the current through the gradient coil system. Moreover, all three coils should generate a magnetic field when the zone 210 is to be shifted along a line extending outside the center 202. This is taken into account by the system's control unit 174 while imposing the variation in time of the currents, for example, by employing appropriate lookup tables. The zone 210, therefore, can be shifted along arbitrarily formed paths through the examination zone.

The signals S received by the sensing coil(s) 150 are applied to an amplifier 180 via a suitable filter 182. The output signals of the amplifier 180 are digitized by an analog-to-digital converter 184 so as to be applied to an image processing unit 186, which reconstructs the spatial distribution of the particles from the signals and the known position of the zone 210 during the reception of the signals S. An image of the sensed particle distribution can be displayed on an appropriate display monitor 188 (or otherwise rendered into a viewable image).

The signal produced from a harmonic field with an additional static field imposed has been characterized as discussed in *Frequency Distribution of the Nanoparticle Magnetization in the Presence of a Static as Well as a Harmonic Magnetic Field*, Medical Physics 35, 1988-1994, 2008, by J. B. Weaver, A. M. Rauwerdink, C. R. Sullivan, I. Baker. The second harmonic produced when there is a static field is larger than the third harmonic providing superior signal to noise. In addition, the size of the static field contributes localization information that contributes to the signal localization. See *Imaging Magnetic Nanoparticles Using the Signal's Frequency Spectrum*, Procedures of SPIE on Medical Imaging, Volume 6916, 6916-35, 2008, by J. B. Weaver, A. M. Rauwerdink, B. S. Trembly, C. R. Sullivan. Further, a combination of harmonic fields produce signal at many specific frequencies which can also be used to contribute localization information.

In medical applications, the ability to attach a nanoparticle to molecular agents that localize in pathology is very promising for both diagnosis and treatment. Also, a highly significant aspect of MPI is the promised sensitivity. Antibody-tagged nanoparticles can be targeted to cancer or other cells in very specific ways but highly selective targeting will generally collect relatively few nanoparticles to a specific location so sensitivity is critical. For example, targeting individual cells would be important to track a metastasis. In view of these promising new medical applications and techniques, it is, thus, highly desirable to refine the above-described system and method for performing MPI to achieve even higher imaging resolution and particle localization accuracy.

More particularly, certain forms of imaging have value in detection and treatment of cancer. Ovarian cancer, for example, is the 5th leading cause of cancer deaths in women. One in 57 women in the US will develop ovarian cancer, however early detection of ovarian cancer offers a 90% cure rate. It is thus highly desirable to provide early detection of ovarian cancer. Current methods for treating ovarian cancer also have several disadvantages. Surgery is typically required to remove the ovaries, or chemotherapy to destroy cells. The chemotherapy generally produces a remission of one to two years, which may be followed by recurrence which is now chemo-resistant. Early detection can thus overcome these disadvantages and the use of advanced imaging techniques can be highly desirable in the diagnosis and treatment of such cancer.

SUMMARY OF THE INVENTION

This invention overcomes the disadvantages of the prior art by providing a system and method that improves the sensitivity and localization capabilities of Magnetic Particle Imaging (MPI) by using combinations of static and oscillating magnetic fields. Combinations of magnetic fields can be used to distribute the signals coming from the magnetic particles among the harmonics in specific ways to improve sensitivity and to provide localization information to speed up or improve the signal-to-noise ratio (SNR) of imaging and/or eliminate the need for saturation fields currently used in MPI. In one embodiment, the signal from particles along a static or slowly varying magnetic field are collected rather than collecting signal only from the field free point, in contrast to the prior art, improving the signal and allowing smaller gradients or better signal-to-noise ratio (SNR) to be achieved. In another embodiment, the second harmonic signal from nanoparticles can be enabled by a localized static field scanned across the object rather than saturating the third harmonic to achieve localization as in prior art. In another embodiment, the static field of an MRI system can be used to create a field offset allowing the signal in the second harmonic to be detected, rather than using only the signal at the third harmonic, to create a combined imaging modality where the particles are imaged using magnetic particle imaging and the anatomy is imaged using conventional magnetic resonance imagery (MRI). In another embodiment, a combination of harmonic fields can be used to place the harmonics at frequencies that are not harmonics of the amplifiers so as to reduce noise and provide extra localization information.

In another embodiment, static field coils can be employed in conjunction with selection and drive coils to provide a static offset to the field-free region so that particles are brought nearer to a saturation level therein. In this manner, greater imaging performance is achieved for a given nanoparticle concentration within a subject. In another embodiment, drive coils can be combined with static field and gradient coils the increase the physical range of the sub-saturation region for nanoparticles. Localization of particles includes observing the distribution of signal among the harmonics generated by the particles in conjunction with the monitoring of the control system that generates waveforms in the magnetic-field coils. In another embodiment, static field and gradient coils can be combined with drive coils in a novel arrangement to increase the range of the sub-saturation region and also to provide various regions with static field offset. Localization of nanoparticles entails observing the distribution of signal among the harmonics and incrementing the static field offset and gradient fields while monitoring this function within the imaging system. In yet another embodiment, the static and field gradient coils are combined with multiple drive coils that each transmit at a discrete frequency or frequencies. In this arrangement, localization of the nanoparticles entails observing the distribution of signal among the frequencies generated by nanoparticles and also observing the combination of various frequencies. A variety of additional arrangements of coils and types of generated magnetic fields can be employed in further alternate embodiments.

In further illustrative embodiments this invention provides a system and method for reading the signal produced by cyclically saturated magnetic particles in a sample so as to provide a measurement of the temperature of those nanoparticles. The spectral distribution of the signal generated provides estimates of the temperature. More particularly, the second and third harmonics increase monotonically with decreasing temperature of the particles and increases monotonically with increasing amplitude of the magnetic field saturating the particles, termed the driving field. Further, the ratio of the fifth and third harmonics is monotonically in the same fashion, however, the ratio of the fifth and third harmonics is independent of particle concentration. Because the harmonics and their ratios change monotonically, the temperature can be found from the harmonics or their ratio. The harmonics also change with particle size distribution. However, by observing the harmonic signals as the amplitude of the driving field is changed a calibration curve can be obtained from the sample of particles in vivo. Therefore, this method of estimating temperature can be used for any size distribution obtained in vivo or even changing size distributions. Indeed, the size distribution of the particles injected might be very different from the size distribution in any given position in vivo but this should not affect the results because the calibration curve can be obtained in vivo at any time by changing the amplitude of the drive field. Indeed, the changes observed in successive calibration curves can be used to estimate other properties such as size distribution and kinetics. In addition, once the binding energy is known, the bound fraction can be monitored longitudinally. Related factors may also be estimated using the procedure of this embodiment—that is, binding energies of the nanoparticles and phase changes of the materials in which the nanoparticles are imbedded. In one embodiment, the particle output voltage of a plurality of harmonics (for example the third and fifth harmonics or other combinations) are correlated to derive the temperature of the particles in accordance with a Langevin function, which accounts for the independent, isotropic spins induced in the heated particles. In an exemplary implementation, the sample being measured resides in a pickup coil, which is surrounded by a drive coil. A balancing coil or other technique can be used to reduce the effect of the driving frequency on measurements. Image gradient coils can be employed with corresponding imaging electronics to provide temperature-dependent images of the particles within the sample, or other internal structure. However, the illustrative systems and methods for measuring temperature can be used without imaging as well.

In an illustrative embodiment, particles with antibodies targeted for cancer cells are injected in the subject. Following binding, a very large applied magnetic field is used to heat the particles in the cancer. The ratio of the harmonics would be used to monitor heating to make sure therapeutic temperatures are achieved in the cancer. In another embodiment, the distribution of the applied fields is changes using temperature information to achieve better therapy. In another embodiment, the harmonics at a constant temperature are used to measure the binding strength of the antibody targeting agents for diagnostic or other purposes including the suitability of therapy. In another embodiment, the harmonics at a constant temperature are used to estimate the number of antibody targeted particles that are bound and the number that are unbound for diagnostic purposes or to know when to start therapy. In another embodiment, the harmonics are used to estimate when a phase change has occurred in the material in which the articles are located.

All of the above-described embodiments can be employed as discrete systems and methods or combined with MPI methods or the imaging methods described here or other imaging methods to create images of the parameters measured. For example, by combining a plurality of systems and methods temperature maps or temperature images can be obtained instead of determining the average temperature in a single volume.

In an illustrative embodiment, a procedure for diagnosing certain cancers in which cells associated with the cancer selectively uptake iron-based nanoparticles overcomes disadvantages of current cancer diagnosis and treatment. The procedure commences by directing a compound/agent containing nanoparticles to be selectively delivered proximate a tumor or cancer site containing cells associated with a cancer. A predetermined period of time is allowed to elapse after infusion of the nanoparticles to allow for the uptake of nanoparticles to the associated cells. These cells are in proximity to the tumorous tissue. Imaging is then performed at predetermined time periods after infusion using an imaging device, typically in accordance with embodiments here, which detects the concentration and levels of nanoparticle uptake in the cells. Analysis of image data provided by the imaging device is then performed to determine the concentration of nanoparticles, thereby indicating the tumor site.

The devices and methods described herein are further applicable to treatment of certain cancers by directing a nanoparticle-based agent to be selectively delivered to a cancer site. After a predetermined period of time to allow for uptake of the nanoparticles to cancer cells, a predetermined field can be applied to the nanoparticles for a sufficient period of time to activate the magnetic cores of the nanoparticles. This induces hyperthermia-mediated destruction of the cells by heating the nanoparticles.

BRIEF DESCRIPTION OF THE DRAWINGS

The invention description below refers to the accompanying drawings, of which.

DETAILED DESCRIPTION

I. Improved Localization and Imaging

Figure 1:
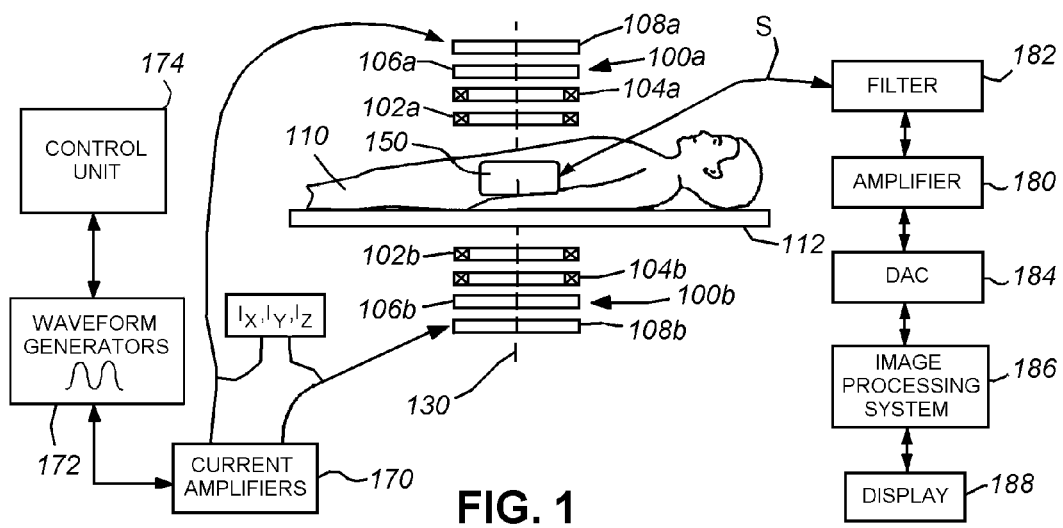
FIG. 1, already described, is a schematic diagram of an exemplary implementation of an MPI system for use in examination of the internal structure of a human patient according to the prior art.
Figure 2:
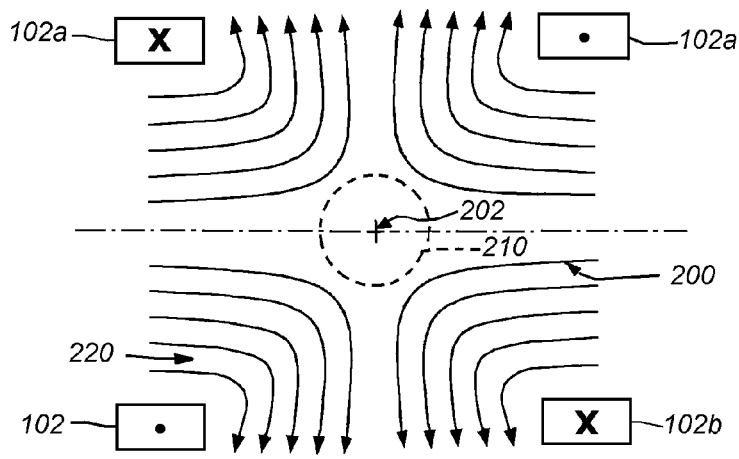
FIG. 2, already described, is a field diagram of the most-adjacent gradient coil to the central field-free zone within the patient/subject.
Figure 3:
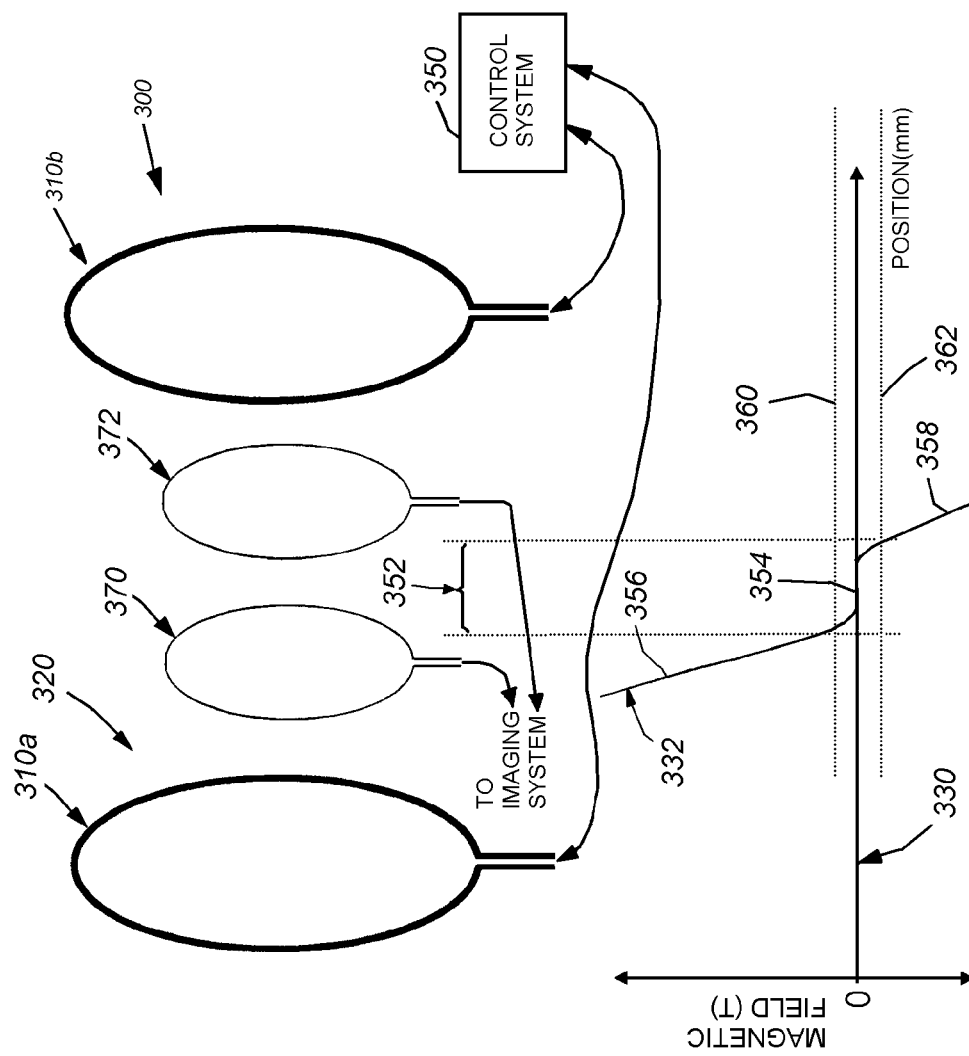
FIG. 3 is highly schematic diagram of the prior art MPI system of FIG. 1 showing the selection and drive coils, sensing coils and detailing the characteristic magnetic field distribution relative to position within the coil arrangement.

Reference is made to FIG. 3 which again describes a simplified MPI system 300 like the MPI system described above with reference to FIG. 1. This system 300 is again discussed and illustrated for the purposes of comparison with the following improved system arrangements described below. The views and graphs depicted are generally two-dimensional, but should be taken to describe the resulting field characteristics in three dimensions. The system 300 consists of groups of drive and selection coils 310a and 310b that define therebetween a magnetic field region 320 that can be characterized by the graph 330. The curve 332 defines the magnetic field across the subject produced by the coils to localize the nanoparticle signal versus position within to the region 320 (e.g. distance from either coil 310a, 310b). As described above, the selection and drive coils are operatively connected with a control system 350. The control system includes appropriate hardware and software (as described above) for amplifying waveforms in the coil windings and generating the desired field-free region 352. This field-free region 352 is exemplified by the flat curve segment 354 which runs approximately along the 0-T value of the vertical axis (magnetic field strength). On either side of the field-free region 352, the field increases in opposing directions with the relative proximity to the adjacent coil (curve segments 356 and 358. Beyond the saturating field, exemplified by horizontal limit lines 360 and 362 about the horizontal (position) axis, the field strength is sufficient to saturate all magnetic particles in these positions, thereby eliminating any signal outside the voxel of interest. Particularly, the prior art MPI system 300 of FIG. 3 operates to impose a large, alternating magnetic field on the nanoparticles so that the induced magnetization is saturated. The saturation creates a distortion in the magnetization giving rise to harmonics which can be detected and which allow the number of nanoparticles to be quantified. Nanoparticles that are saturated by a harmonic magnetic field only produce odd harmonics. The system contemplates imaging of the nanoparticles using a static field to saturate all the particles outside the given volume, and as that volume is swept across the subject, an image can then be formed by sensing the harmonics of the swept field using the sensing coils 370, 372 in combination with the above-described imaging system/display.

Hence, the signal from particles along a static or slowly varying magnetic field are collected rather than collecting signal only from the field free point, in contrast to the prior art, thereby improving the signal and allowing smaller gradients or better signal-to-noise ratio (SNR) to be achieved.

Figure 4:
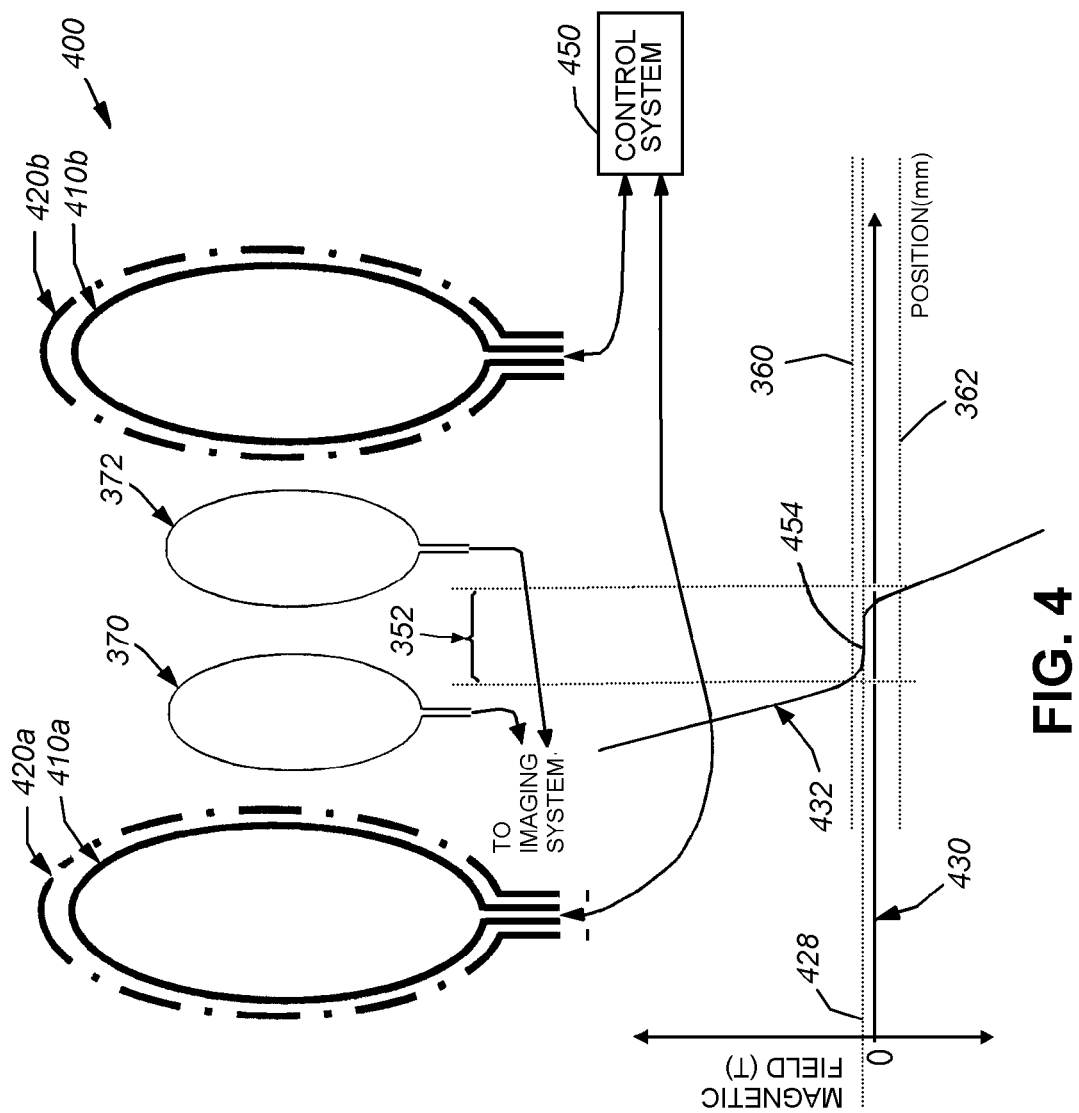
FIG. 4 is a schematic diagram of an improved MPI system and generated magnetic field distribution employing a static field offset according to an embodiment of the invention.

An improved MPI system 400 in accordance with a novel embodiment of this invention is shown in FIG. 4. In this embodiment, the selection and drive coils 410 are essentially the same as the system 300 above. However, they have been supplemented with respective static field coils 420a, 420b that, under direction of the control unit 450 generate a static field offset (horizontal line 428 on the related graph 430). This static field offset moves the horizontal segment 454 of the field strength-versus-position curve 432 away from the 0-T value of the vertical axis. In one embodiment, the static field can be generated by MRI coils.

The static field of an MRI system can be used to create a field offset allowing the signal in the second harmonic to be detected, rather than using only the signal at the third harmonic, to create a combined imaging modality where the particles are imaged using magnetic particle imaging and the anatomy is imaged using conventional magnetic resonance imagery (MRI).

Note that a combination of harmonic fields can be used to place the second and third harmonics at frequencies that are not harmonics of the system's sensing amplifiers so as to reduce noise and provide extra localization information.

This static magnetic field nearly saturates the nanoparticles allowing a much smaller alternating magnetic field to thereby saturate the nanoparticles (i.e. the line 428 is moved closer to the upper saturation field 360). High-frequency alternating fields can be used with relatively low power producing relatively high power because the signal is proportional to frequency or alternatively or in addition a swept static field could be employed. Most of the nanoparticles can be saturated many times per unit time, by a sinusoidal current, obtaining both large numbers of nanoparticles saturated and a higher frequency of saturation so the signal is increased both of which increase the signal produced. Note that the use of static field coils can also be employed with others embodiments of the invention as described further below.

Figure 5:
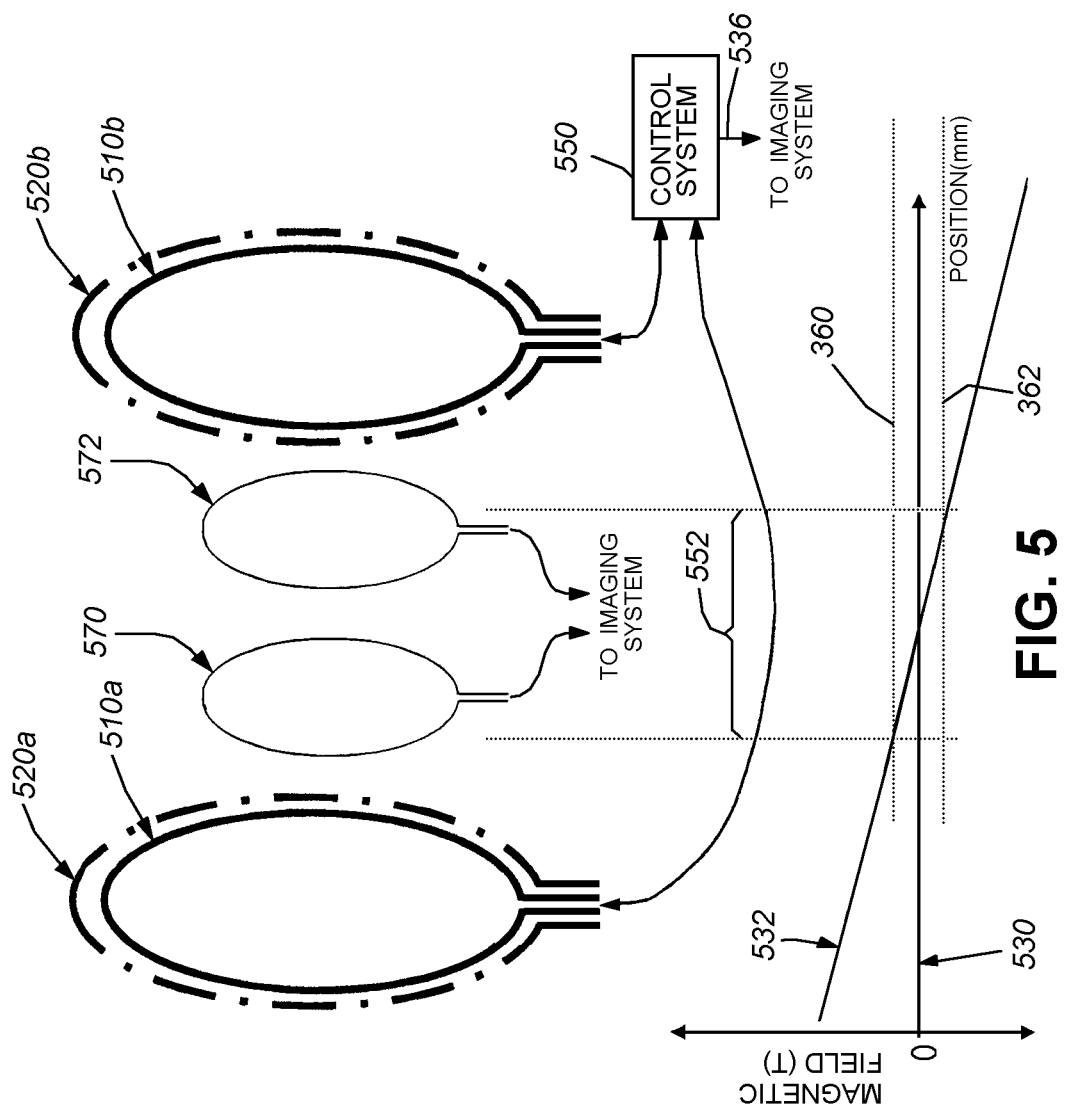
FIG. 5 is a schematic diagram of an improved MPI system and generated magnetic field distribution employing an enlarged region in which a signal is generated according to another embodiment of the invention.

In another embodiment, shown in FIG. 5, the system 500 includes selection and drive coils 510a, 510b similar to those described above as well as static field and gradient coils 520a and 520b, all of which are controlled by a control system 550 that generates appropriate amplitudes and waveforms in the coils. In this embodiment, the static field offset generated by the coils 520a, 520b, in combination with the gradient serves to enlarge the region 552 from which the nanoparticles generate a signal. Also, it is contemplated that combinations of static and time-varying magnetic fields from the coils can be used to produce harmonics at a variety of frequencies, phases, amplitudes and directions that can be used to localize the nanoparticles or increase the signal generated from the nanoparticles. As such, this implementation adds even (primarily $2^{nd}$) harmonics as well as odd (primarily $3^{rd}$) harmonics, thereby partly increasing the signal. The additional harmonics allows the imaging system (via a link 536) to better localize a signal by observing the distribution of the harmonics along the gradient. In particular, localization entails observing (with the sensing coils 570, 572) the distribution of harmonics and difference signals; e.g., those described in *Microwave Engineering* by Paul Pozar, John Wiley and Sons, pages 503-504, the teachings of which are expressly incorporated herein by reference. The total signal-per-unit time collected increases in this approach because the larger region 552 (see also graph 530 and the flatter curve 532) is employed. In addition, the signal increases because parts of that region are provided with static field offsets that increase the signal from the particles.

Note that a variety of particle-localization techniques can be employed in accordance with various embodiments. For example, multiple-frequency harmonic fields can produce a signal at the difference between the two frequencies and at a variety of other frequencies. When the frequency content changes with position, because one of the alternating field's strengths change with position, the position of the nanoparticles can be isolated by the signal strength at each frequency. Similarly, the phase of the harmonic fields can be used to localize the nanoparticles as well. The uniform and spatially varying magnetic fields can be arbitrary functions of time including, but not limited, to sinusoids, harmonic, square and triangular waves.

Figure 6:
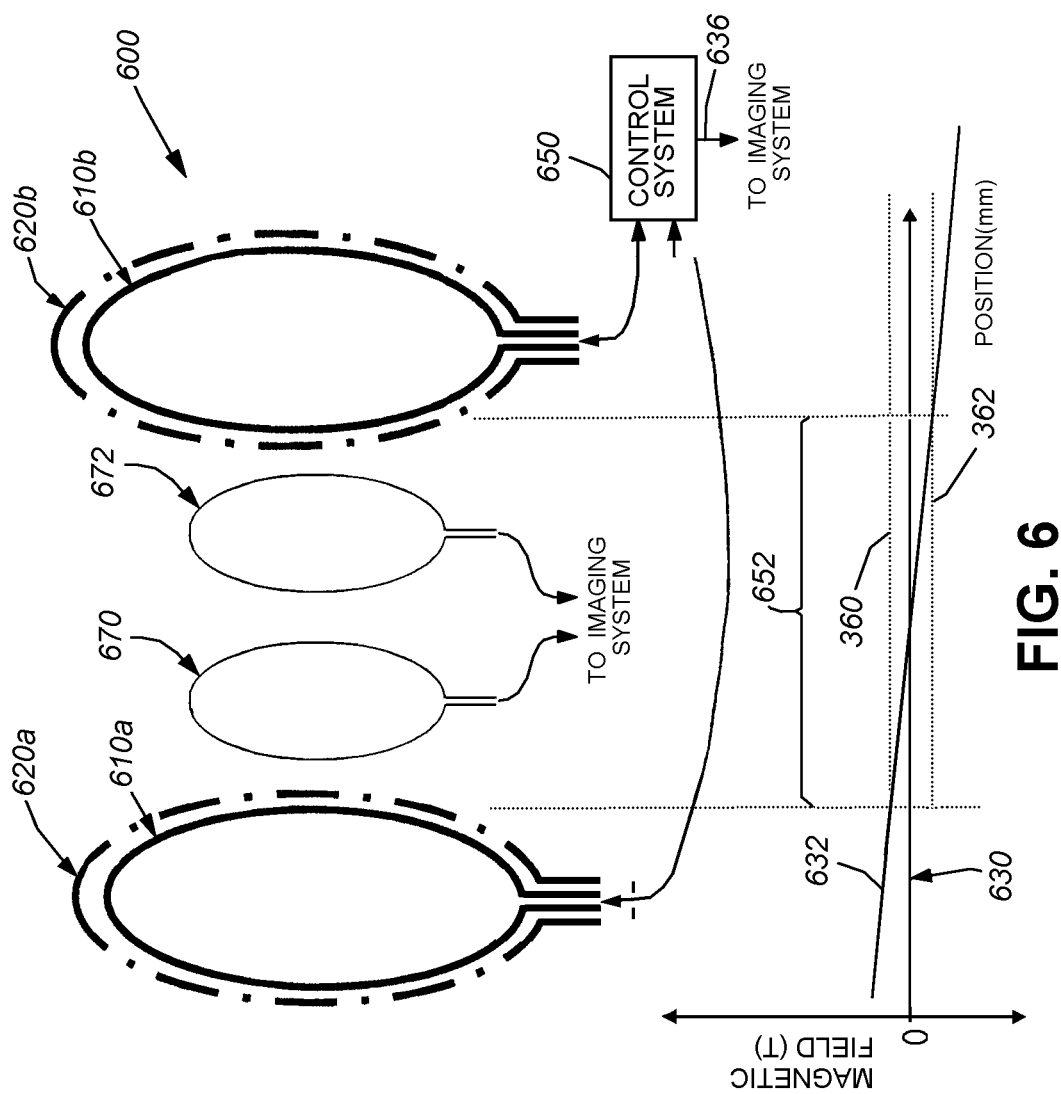
FIG. 6 is a schematic diagram of an improved MPI system and generated magnetic field distribution employing a signal generated from the entire region between drive coils according to yet another embodiment of the invention.

Referring now to FIG. 6, an embodiment of an MPI system 600 is shown, that may be free of the particular coil implementations of, for example, the above-incorporated U.S. Patent Application No. 2003/0085703. The system 600 is generally similar in function to system 500 above, in that it includes drive and selection coils 610a, 610b, as well as static filed and gradient coils 620a, 620b. These are controlled to deliver waveforms at a given amplitude to various coils by the control system 650. In this embodiment, the generated nanoparticle signal is generated over substantially the entire region 652 (see also graph 630 and curve 632) between coils 610a, 610b, 620a, 620b, because the coils have now been arranged to create sub-saturation-level fields (within graph field-strength limit lines 360, 362) across this entire region 652. This arrangement generates identifiable even and odd harmonics are created in the particle signal in a manner described above with reference to the system 500. The generation can be monitored by the imaging system through a link 636 with the control system 650.

More particularly, in this embodiment, localization of the signal from nanoparticles entails observing (with the sensing coils 670, 672) the distribution of harmonics and difference frequencies, and incrementing (with control system 550) the static field offset and gradient field (via coils 520a, 520b) to achieve different predetermined values. As such the total signal-per-unit time collected is significantly increased both due to the significantly larger region 652 and because parts of the region have static offsets.

Figure 7:
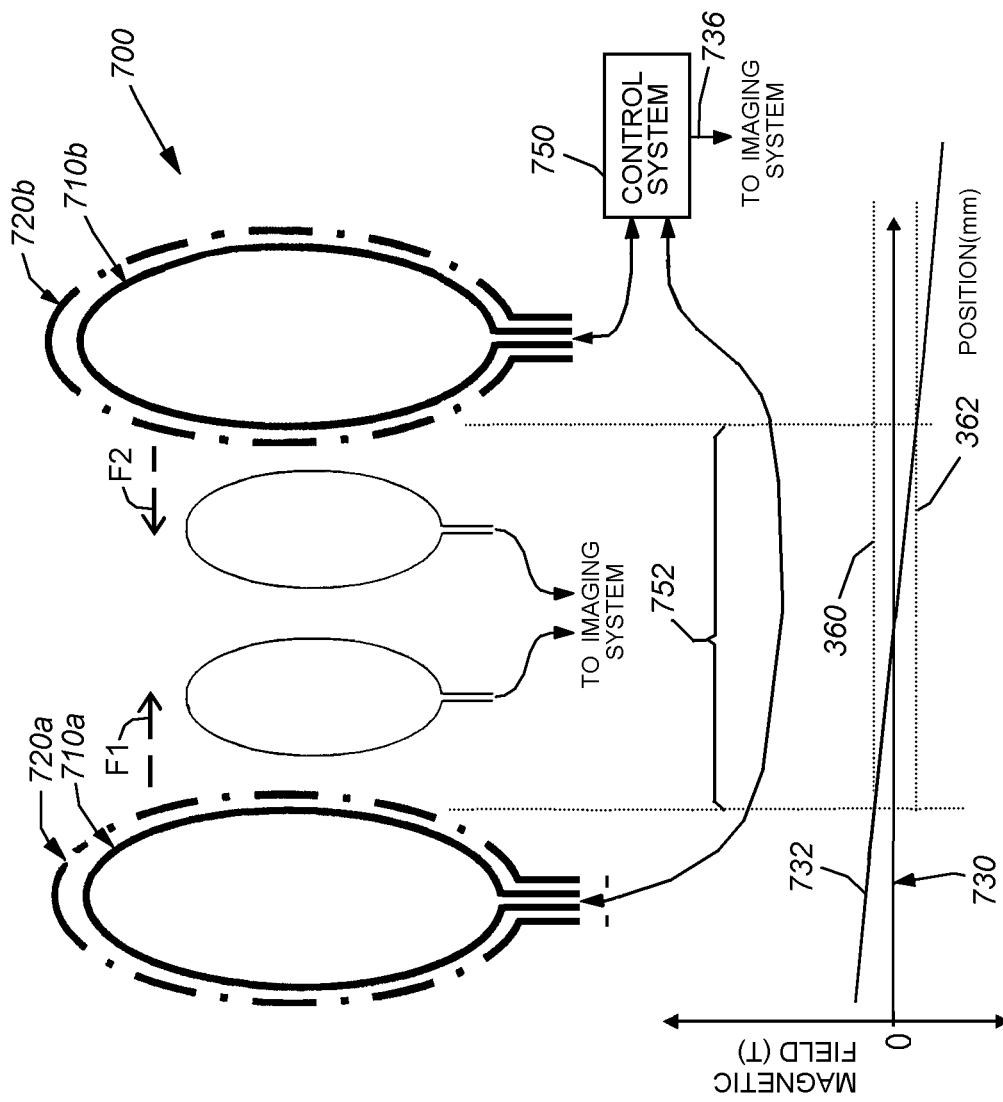
FIG. 7 is a schematic diagram of an improved MPI system and generated magnetic field distribution employing a signal generated from the entire region between drive coils, and the drive coils each generating a different frequency, according to yet another embodiment of the invention.

FIG. 7 details another embodiment of an MPI system 700 in accordance with this invention that may employ arrangements of components similar to those of the system 600 described above. In this embodiment, the signal is also desirably generated across the entire region 752 between coils (as denoted by the graph 730 and curve 732). Notably, in this embodiment, the control system 750 drives each of two drive coils 710a and 710b at different frequencies (F1 and F2, respectively). Static and gradient coils 720a, 720b, like those described above, are also employed and function similarly to the systems described above. The two frequencies F1 and F2 generated by the respective drive coils 710a, 710b result in the generation of signal at a series of interference frequencies that depend on the relative amplitude of the drive fields at the two frequencies. More coils at different frequencies can be added to further localize the nanoparticles.

Localization of the signal from nanoparticles within the subject entails observing the distribution of harmonics and the combinations of frequencies, which is characteristic for each position relative to the drive coils and gradient coils. The characteristic combination of signal strengths for each position allows the position of the nanoparticles to be identified by inverting the measured distribution of signal strengths. This allows for more accurate resolution of particles as the frequencies generated by the coils are correlated via the control system link 736 with the imaging system. In addition, as described above, the larger region and static offset provided by the coil arrangement of this embodiment desirably provides a higher signal strength from nanoparticles.

It should be apparent that a variety of arrangements and combinations of magnetic-field-generating components can be provided to effect imaging in accordance with alternate embodiments of this invention. For example, nanoparticles can be imaged with the subject on a fixed stage that is then moved into an MRI device for imaging of the anatomy. An MPI system in accordance with this invention is mounted in conjunction with the MRI and the subject is infused with a low concentration of nanoparticles. This hybrid or combination system, thus, employs the MRI to image the anatomy and the MPI to image the nanoparticles in the very low concentrations. The same subject-support structure/stage can be used to facilitate co-registration between the two systems. In particular, the acquired images of each system can be co-registered so the nanoparticle image is co-registered with the MRI anatomy in the imaging system. This arrangement can therefore be used as PET-CT systems are employed clinically. The method of increasing the signal from the nanoparticles described above for systems 500 and 600 is achieved if the correct place in the static field is used for magnetic particle imaging.

II. Temperature Sensing

It is recognized that nanoparticles can be heated by remote mechanisms, including electromagnetic excitation (i.e. hysteresis). The heating of magnetic particles, infused into a local region of a patient's body can be used in the important application of hyperthermia treatment. That is a localized region of the body is heated to eliminate thermally sensitive cells and tissues, such as those often encountered in various forms of cancer. By understanding how magnetic particles react under varied temperature, one can also derive information and images of the particles' relative temperature and the temperature distribution within the body or other internal structure. Other characteristics, such as phase change can also be imaged and mapped. More particularly, the signal produced by cyclically saturated magnetic nanoparticles can provide a measurement of the temperature of those nanoparticles. The spectral distribution of the signal generated provides estimates of the temperature. Related factors may also be estimated: binding energies of the nanoparticles and phase changes or stiffness of the materials or cells to which the nanoparticles are connected. Note also that there are many other possible applications for measurement of temperature in addition to those in the field of medical hyperthermia treatment.

Figure 8:
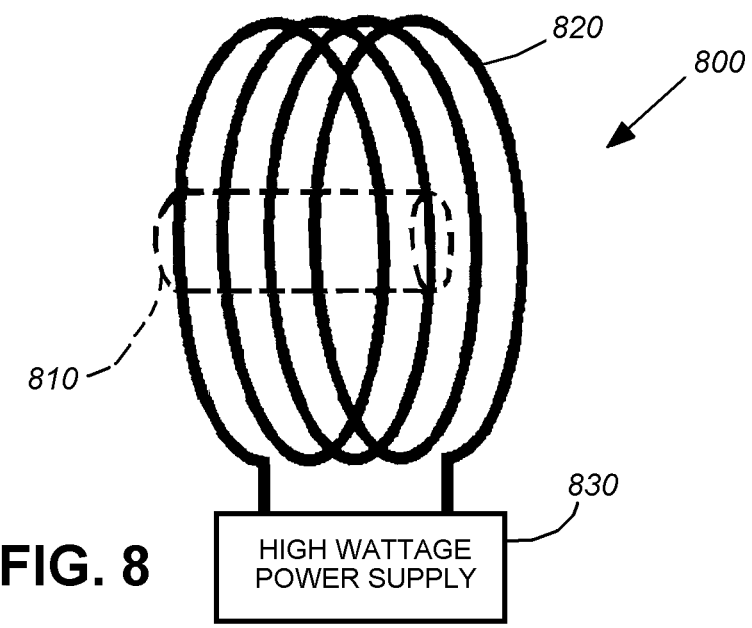
FIG. 8 is a schematic diagram of an alternating current heating coil for activating a sample having magnetic nanoparticles according to this invention.

FIG. 8 is a schematic diagram detailing a generalized arrangement 800 for heating infused magnetic nanoparticles contained in a sample 810 or other internal structure (shown in phantom) according to an embodiment of this invention. The "sample" as shown and described herein can be a simple container with a heatable medium, or a more complex structure, such as the above-described human body. The term "subject" can be used as an alternative to the word "sample". This basic example includes only the heating element (no imaging components), which is a liquid-cooled coil 820 that is interconnected to an alternating current power supply having a sufficient power level and frequency to generate the desired heating effect in the sample 810.

Figure 9:
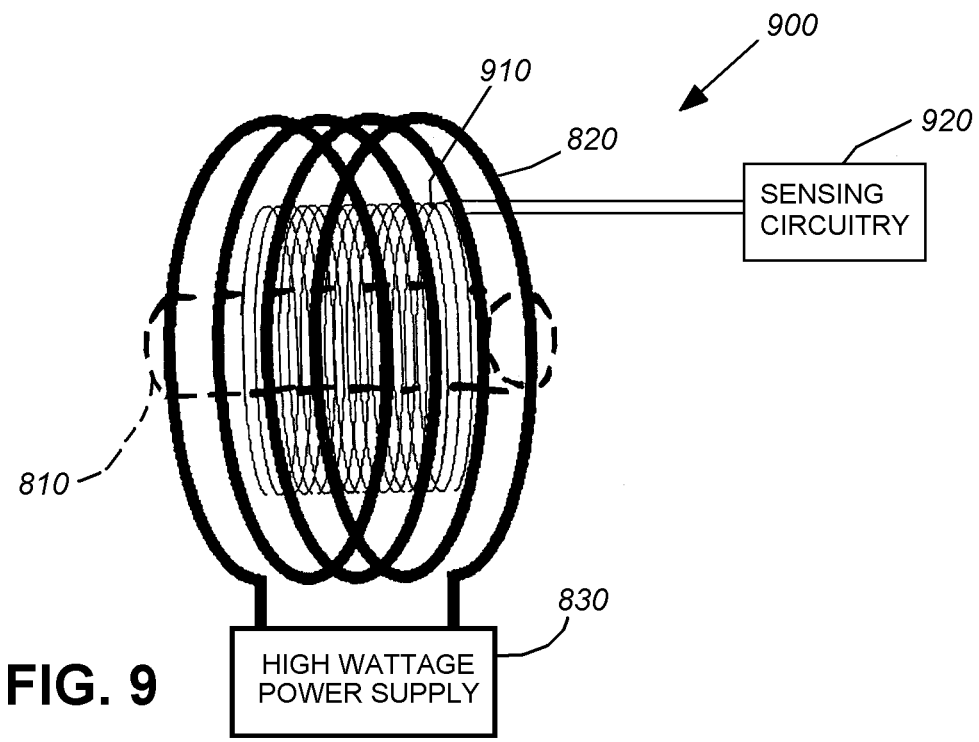
FIG. 9 is a schematic diagram of the alternating current heating coil of FIG. 8 in combination with a coaxial pickup coil that senses output signals in the nanoparticles of the sample in response to excitation by the heating coil according to an illustrative embodiment.

As shown in FIG. 9, the arrangement 900 includes a pickup coil 910 located coaxially between the nanoparticles heating coil 820 and the nanoparticle-containing sample 810. Note that the heating coil 820 is exemplary and a variety of alternate techniques can be employed to heat nanoparticles within an internal structure in alternate embodiments of the invention. This arrangement is a basic embodiment of a temperature-measurement system in which the principles of this invention can be applied to allow interconnected sensing circuitry 920 (operating in accordance with the procedures described below) to measure the temperature of the nanoparticles of the sample 810 at predetermined locations therein.

Figure 10:
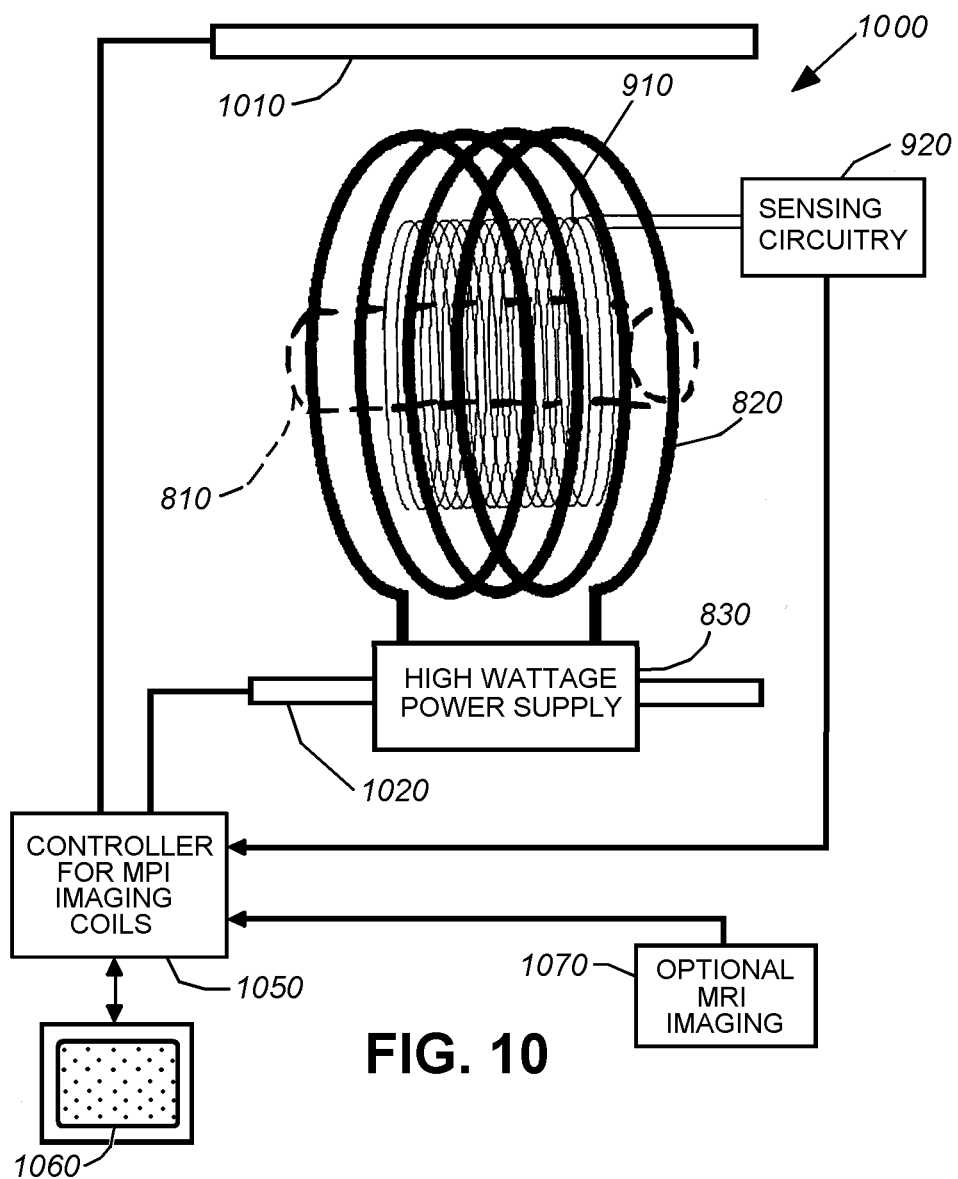
FIG. 10 is a schematic diagram of the alternating current heating coil and pickup coil of FIG. 9, and further including imaging coils and associated imaging electronics for forming an image of the heated nanoparticles within the sample, according to an embodiment of this invention.

Referring now to FIG. 10, an MPI imaging system according to a conventional implementation, or an improved version as contemplated herein, is incorporated into the temperature measurement arrangement 900 of FIG. 9. The resulting arrangement 1000 includes a pair of opposed MPI imaging field coils 1010 and 1020 adapted to generate an image of the excited nanoparticles (which can be also acted upon by other MPI gradient coils (not shown) of conventional or improved design). The image is processed by an appropriate controller 1050, which interacts with the sensing circuitry 920 of the pickup coil 910, as shown. In this manner, the sensed localized temperature and temperature variation can be mapped with respect to an image that can be viewed on an interconnected display 1060.

The measurement of temperature by the controller 1050 and sensing circuitry 920 relies upon a model for the hysteresis curve exhibited by the magnetically excited nanoparticles in the sample 810. This model describes the magnetization of the nanoparticles, which is what produces the underlying signal that is observed by the pickup coil 910. The model used for independent, isotropic spins is a Langevin function. Even in systems where the superparamagnetic model is not strictly applicable, the model provides a good estimate of temperature. The basis for the model is that thermal motion prevents the nanoparticles from aligning perfectly with respect to the applied magnetic field (produced via the coil 820). The result is a balance between the forces induced by the applied magnetic field and thermal activity of the nanoparticles.

Figure 11:
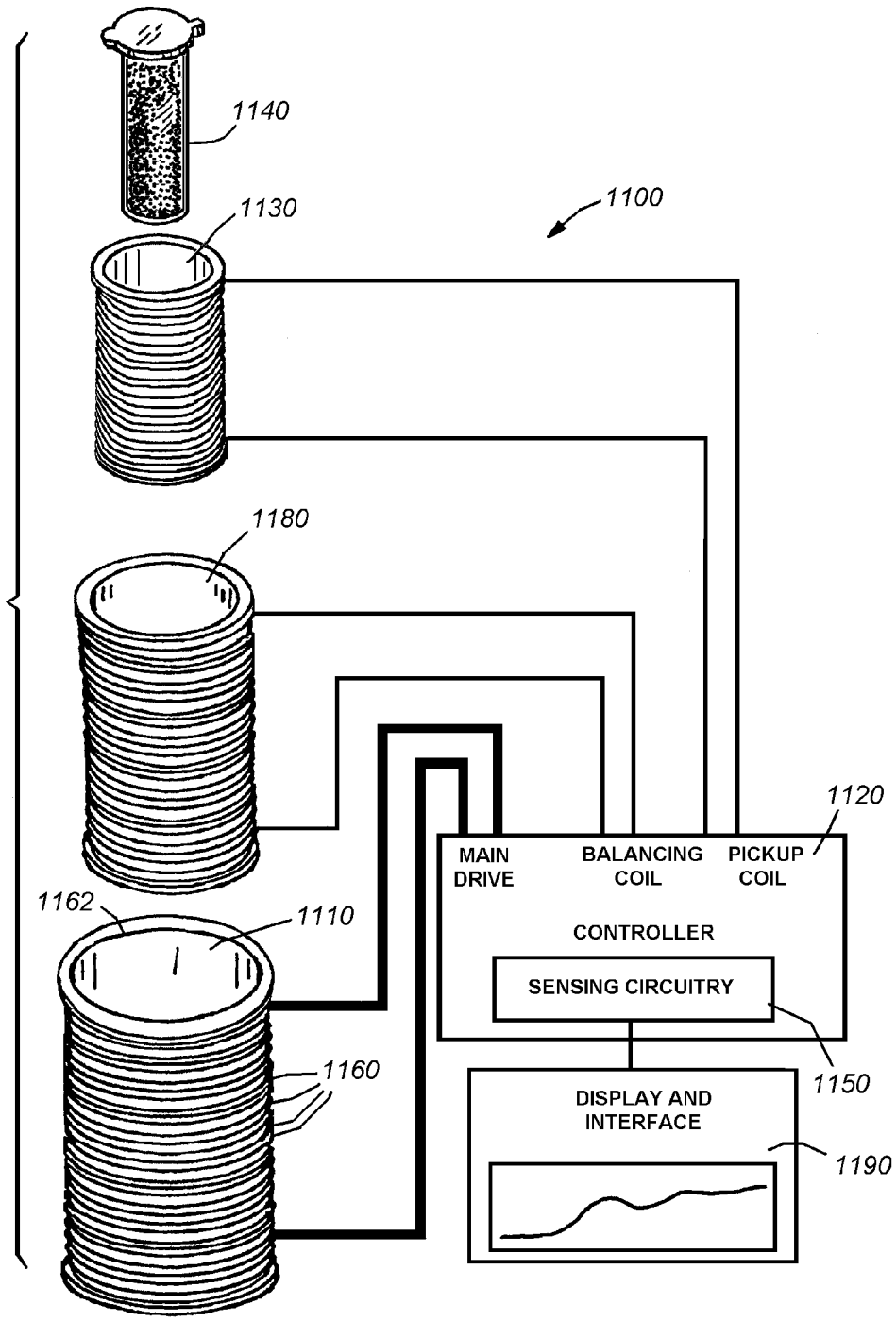
FIG. 11 is an exploded perspective view of an arrangement for sensing the temperature of heated nanoparticles in a sample consisting of a coaxial drive, balancing and pickup coil, and associated sensing/control circuitry according to an illustrative embodiment.
Figure 12:
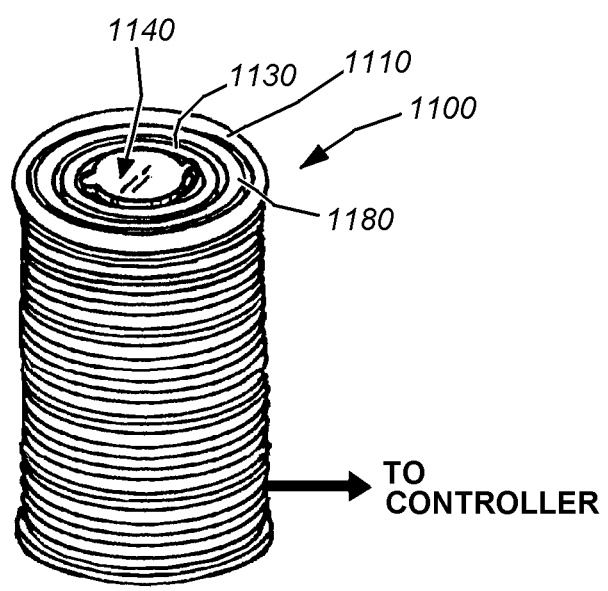
FIG. 12 is a perspective view of the assembled temperature-sensing arrangement of FIG. 11 with the sample inserted thereinto.

An exemplary arrangement 1100 employed to test the temperature-measurement principles described herein (for example, as provided in FIG. 9) is shown in respective exploded and assembled views in FIGS. 11 and 12. This example comprises resonant coil 1110 that drives the magnetization harmonically using an appropriate alternating current drive circuit that is part of a controller 1120. The receive circuit is a pickup coil 1130 that resides coaxially within the drive coil 1110. The pickup coil 1130 records the voltage induced in the particles by the magnetization. In this embodiment, the particles are placed in a magnetically-transparent container 1140 that resides coaxially within the pickup coil 1140. In alternate embodiments other techniques for suspending a sample or sample within the pickup coil 1140 can be employed. The signal voltage at each harmonic frequency is measured by a sensing circuitry 1150 within the controller, which is interconnected to the pickup coil. The drive coil 1110 is characterized as a solenoid resonant coil having (in this example) approximately 1400 wire turns 1160 along a cylinder which is approximately 10 cm long. The sinusoidal current is produced by an audio amplifier fed by a signal generator within the controller circuit 1120. The sinusoidal voltage is set at the resonant frequency of the coil 1110. In this embodiment, the pick up coil 1130 resides coaxially inside both the drive coil 1110 and a series-connected balancing coil 1180 placed at the end of the drive coil 1110 and coaxially between the drive coil and the pickup coil. The balancing coil is optional in alternate embodiments. In this example, the balancing coil 1180 serves to reduce the voltage at the drive frequency so the signals generated by the nanoparticles can be amplified sufficiently to be recorded by the controller 1120. Graphical and/or alphanumeric readings of temperature can be provided by an interconnected display and user interface 1190 of any acceptable type, which is connected to the controller 1120 and sensing circuitry 1150.

In a group of magnetically activated particles, the characteristic hysteresis curve determines the magnetization induced in a material by a time-varying magnetic field. Even for relatively high concentrations of suspended nanoparticles, such as those present in magnetic fluids (ferrofluids for example), the magnetization is well-defined by treating the particles as independent, isotropic spins governed by a combination of statistical thermal fluctuations and the applied magnetic field. See R. Kaiser and G. Miskoloczy, *Magnetic Properties of Stable Dispersions of Subdomain Magnetite Particles*, J. Appl. Phys. 41 (1970) 1064-72, which is incorporated by reference herein as further background information. It follows that suspensions of nanoparticles should be accurately described by the same theory because the particles are more disperse and are small enough to be characterized as a single magnetic domain. The hysteresis curve for a group of identical nanoparticles should be well-described by a Langevin function. See Kaiser. Hence, the magnetization, M, for a harmonic driving field is:

$$M = M_0 \left\{ \cosh\left(\frac{vM_0H}{4\pi kT}\right) - \left(\frac{vM_0H}{4\pi kT}\right)^{-1} \right\} \quad \text{Eq. 1}$$

where M is the magnetization, $M_0$ is the bulk magnetization, v is the volume of the particle, H is the applied field, k is the Boltzmann constant and T is the absolute temperature. In this case, the applied field consists of the sinusoidal field, $H_s = H_0 \sin(\omega t)$, and the constant bias field (generated by bias coils), $H_{bias}$:

$$M = M_0 \left\{ \cosh\left(\frac{vM_0(H_0\sin(\omega t) + H_{bias})}{4\pi kT}\right) - \left(\frac{vM_0(H_0\sin(\omega t) + H_{bias})}{4\pi kT}\right)^{-1} \right\} \quad \text{Eq. 2}$$

Note that it is useful to think about the effects of temperature as an effective field which scales the applied field:

$$M = M_0 \left\{ \cosh\left(\frac{H_0\sin(\omega t) + H_{bias}}{H_{TE}}\right) - \left(\frac{H_0\sin(\omega t) + H_{bias}}{H_{TE}}\right)^{-1} \right\} \quad \text{Eq. 3}$$

where $$H_{TE} = \frac{4\pi kT}{vM_0} \quad \text{Eq. 4}$$

is the temperature equivalent field. The value $H_{TE}$ scales the applied field in the above Eq. 3, so for a large value of $H_{TE}$, a correspondingly larger applied field is required to influence the nanoparticles. $H_{TE}$ is larger for smaller particles, and also for particles with a smaller bulk magnetization or for particles having higher temperatures. The thermal disordering of the nanoparticle magnetizations, reflected by $H_{TE}$, reduces the ability of the applied field to align the individual nanoparticle magnetizations into a macroscopic effect.

It should be noted that collections of sensed particles of different sizes are described by multiple Langevin functions, and although the characteristic properties of the hysteresis curve remain the same, the shape of the curve depends on the distribution of sizes and properties. The size distribution is generally normally distributed. The primary effect of the particle radius is on the corresponding particle volume of the nanoparticle, v, but the particle size also affects the coercive field. The coercive field is a measure of the phase of the magnetization relative to the applied field and does not influence the shape of the hysteresis curve, just the translation of it which can be represented as a time shift in Eq. 3 above. A time shift represents a phase change in the frequency domain so the effect of nanoparticle size on the coercive field causes interference between the magnetizations of the nanoparticles of different sizes.

The most stable technique for estimating $H_{TE}$, and therefore the particle temperature, is by employing a least squares fit of the particle's signal at three or more harmonic frequencies to those calculated by a simple Langevin function. There exists no redundancy between signals, and if a significant signal is observed at all the frequencies, the temperature estimates at each harmonic will be reasonably stable with respect to each other. Hence the calculation of temperature based upon a plurality of harmonics allows for a fairly accurate and reliable estimate of actual particle temperature.

Figure 13:
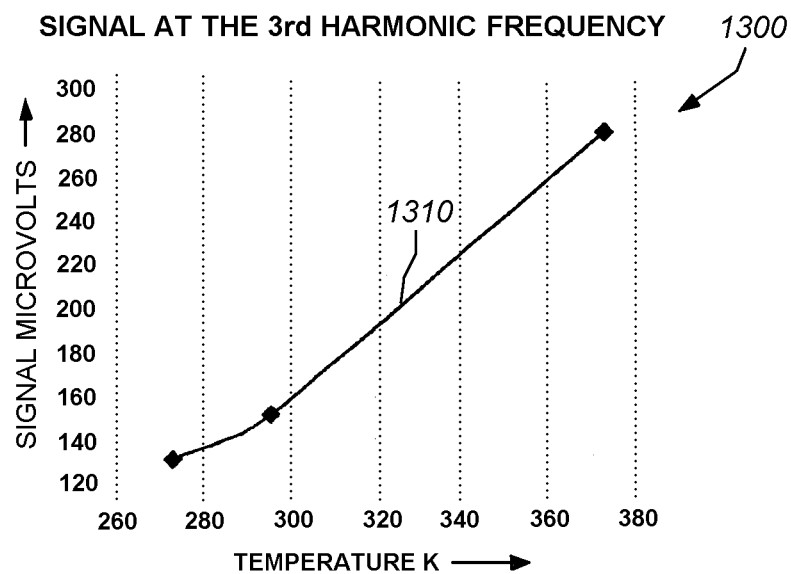
FIG. 13 is a curve of an exemplary output-voltage-to-temperature curve for the third harmonic of the nanoparticle output signal sensed by the pickup coil of the illustrative temperature-sensing arrangement.
Figure 14:
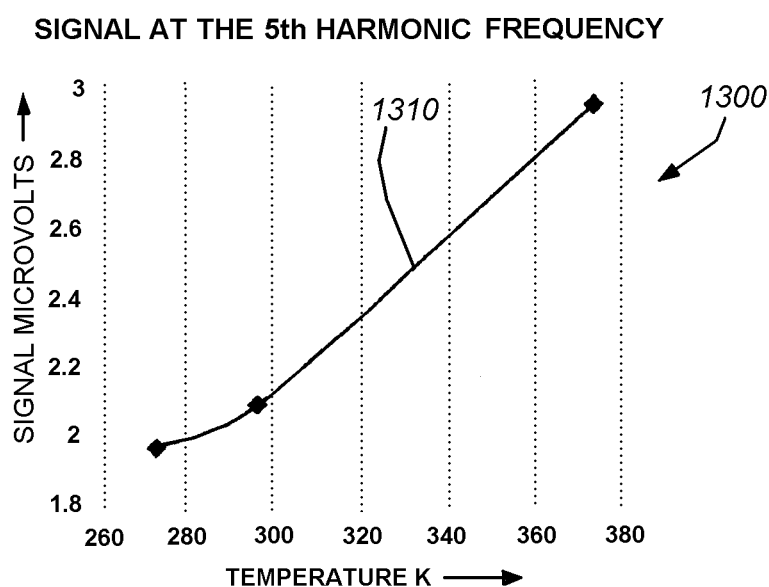
FIG. 14 is a curve of an exemplary output-voltage-to-temperature curve for the fifth harmonic of the nanoparticle output signal sensed by the pickup coil of the illustrative temperature-sensing arrangement.

Referring to the exemplary curves of FIGS. 13 and 14 (1300 and 1400), the respective signal outputs for the third and fifth harmonics in a functional example (refer to FIGS. 11 and 12 above). Each curve 1310 and 1410 respectively plots the measured signal in microvolts versus the absolute temperature (Kelvin) for the measured particles. As shown, the signal at each harmonic frequency increases generally with temperature, thereby providing the requisite technique to measure nanoparticle temperature according to this invention. Note that the curves 1310, 1410 are highly similar in slope and profile and relatively linear at higher temperatures in which the particles will normally be measured. The curve 1310 for the third harmonic is nearly two orders of magnitude greater than the curve 1410 for the fifth harmonic, allowing for separation of the respective signals.

Note that the second and third harmonics increase monotonically with decreasing temperature of the particles and increases monotonically with increasing amplitude of the magnetic field saturating the particles, termed the driving field. Further, the ratio of the fifth and third harmonics is monotonically in the same fashion, however, the ratio of the fifth and third harmonics is independent of particle concentration. Because the harmonics and their ratios change monotonically, the temperature can be found from the harmonics or their ratio. The harmonics also change with particle size distribution. However, by observing the harmonic signals as the amplitude of the driving field is changed a calibration curve can be obtained from the sample of particles in vivo. Therefore, this method of estimating temperature can be used for any size distribution obtained in vivo or even changing size distributions. Indeed, the size distribution of the particles injected might be very different from the size distribution in any given position in vivo but this should not affect the result because the calibration curve can be obtained in vivo at any time by changing the amplitude of the drive field. Indeed, the changes observed in successive calibration curves can be used to estimate other properties such as size distribution and kinetics. In addition, once the binding energy is known, the bound fraction can be monitored longitudinally.

Figure 15:
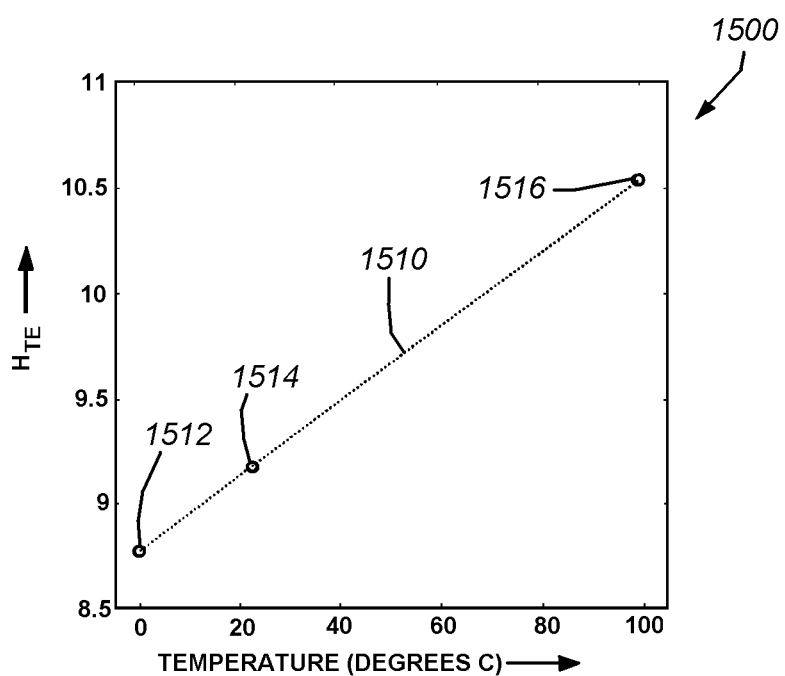
FIG. 15 is an exemplary curve of the relationship between the field value $H_{TE}$ with respect to actual nanoparticle temperature.

An example of a resulting estimate of $H_{TE}$ is shown in FIG. 15, which is a graph 1500 of a curve 1510 which plots measured points 1512, 1514 and 1516 for the measurement $H_{TE}$ versus Temperature (in degrees C.) in the exemplary implementation. As depicted, the $H_{TE}$ estimate as a function of temperature increases linearly with temperature as suggested by Eq. 4. The spectrum at zero-bias field was used to estimate the $H_{TE}$ and the Langevin function modeling $H_{TE}$ is shown. The Langevin function matches the spectra well at low bias fields only showing that the particle output signal is dominated by larger nanoparticles at low bias fields.

Estimates of the ratio $H_o/H_{TE}$ can also be generated from the ratio of the signals at the third and the fifth harmonic frequencies with no bias field and $H_{TE}$ itself can be estimated if $H_o$ is also known and the range of $H_{TE}$ is known. The ratio of the signal at the third and fifth harmonic frequencies is independent of $M_o$ and decreases monotonically between zeros in the fifth harmonic with increasing ratio $H_o/H_{TE}$, so the ratio $H_o/H_{TE}$ can be obtained uniquely from the ratio of the signals between harmonics. $H_{TE}$ includes the effect of nanoparticle volume, v, and the bulk magnetization, $M_o$, which completely characterizes the nanoparticles for MPI if the nanoparticles are of a single size. However, once these parameters are known at one temperature, changes in temperature can be measured by measuring $H_{TE}$, which is directly proportional to temperature. The accuracy of these temperature estimates depends on the size distribution of the nanoparticles.

III. Applications in Diagnosis and Treatment of Certain Cancers

The systems, methods and principles above can be used to selectively target certain types of cancer cells. An infusion via, for example, injection of a compound containing nanoparticles allows for imaging to be used in diagnosis, and where applicable, treatment of certain cancers. As described in greater detail below with respect to the clinical trials, the injected nanoparticles are absorbed by phagocytes or are selectively targeting phagocytes. The phagocytes then collect in the cancer/tumor site, thereby producing an increased concentration of nanoparticles within the cancer site. Advantageously, this allows for very early detection of tumor masses and cancer cells. The phagocytes (phagocytic leukocytes) are types of cancer cells collect at the site of the malignancy and can be followed by detecting levels of nanoparticle uptake to the cells for imaging to assist in diagnosis.

Early detection of ovarian cancer, for example, can be accomplished by following cells in the peritoneum as they collect at the site of the malignancy. Ovarian cancer is an ideal malignancy for diagnostic nanotechnologies described herein because it is initially restricted to the peritoneal cavity for imaging and/or treatment purposes. This allows for the nanoparticle agent to be applied directly into the peritoneal cavity. Direct application into the peritoneum avoids the need for systemic nanoparticle delivery required in other forms of cancer, and bypasses the problem of nanoparticle sequestration in the lung and liver. In advanced ovarian cancer, the ascetic fluid contains many inflammatory cells and irrigates multiple peritoneal tumor masses in which tumor-associated phagocytic leukocytes accumulate at the growing edge. Therefore, intraperitoneally administered nanomaterials, including superparamagnetic iron oxide nanoparticles as described herein, are uptaken by the phagocytes. However, while the illustrative procedure is applied to organs and tissues where particles are not generally free to migrate throughout the body, it is expressly contemplated that the techniques herein can be adapted for use in a variety of organs using appropriate mechanisms to concentrate or control the migration of nanoparticles, so that targeted regions are more particularly provided with nanoparticle populations.

A. Intraperitoneal Injection

Figure 16:
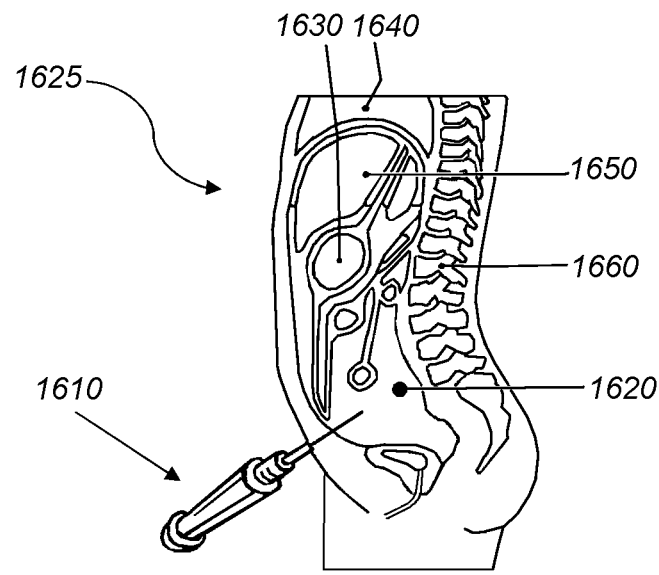
FIG. 16 is a side cross-sectional view as taken through a patient, showing an exemplary technique for intraperitoneal injection of an agent using a needle, according to an illustrative diagnosis and treatment procedure.

In one exemplary procedure for detecting a tumor mass, a compound/agent containing nanoparticles is directed into the peritoneal cavity of a patient, as shown, or example, in FIG. 16. The agent is administered directly via a needle 1610 into the peritoneal cavity 1620 of a patient 1625. The injection into the peritoneal cavity allows for monitoring and imaging of the nanoparticles to detect, for example, ovarian cancer. The agent administered can include dextran coated iron oxide nanoparticles in an illustrative embodiment. Any appropriate coating for iron oxide nanoparticles can be provided in alternate embodiments. The nanoparticles are suspended in saline or water for administration purposes, but other agents or combinations thereof are expressly contemplated.

As described in greater detail below, specific leukocyte cells uptake the nanoparticles in greater concentrations, thereby allowing detection of the nanoparticles for imaging, diagnosis and treatment purposes. For example, immature dentritic cells can absorb magnetic nanoparticles injected into the peritoneum and collect in the ovary with the malignancy. Alternatively, the cells can be withdrawn, loaded with nanoparticles and reintroduced to collect at the malignancy. Several methods of detecting the levels of nanoparticles collected at the malignancy can be employed including but not limited to MRI, MPI, optical imaging, nuclear medicine and nanoparticle spectroscopy.

B. Uptake Rate

Notably, the nanoparticles are absorbed into the phagocytes at an increased rate in individuals with cancer because of the increased activity of the immune system. The rate at which the nanoparticles are absorbed can be measured using the spectroscopy described in this application. More specifically, the relative size of the harmonics derived during spectroscopy can be employed, using techniques in accordance with ordinary skill, to estimate bound fraction which in this case is the fraction absorbed by the phagocytes.

C. Intraperitoneal Imaging

Figure 17:
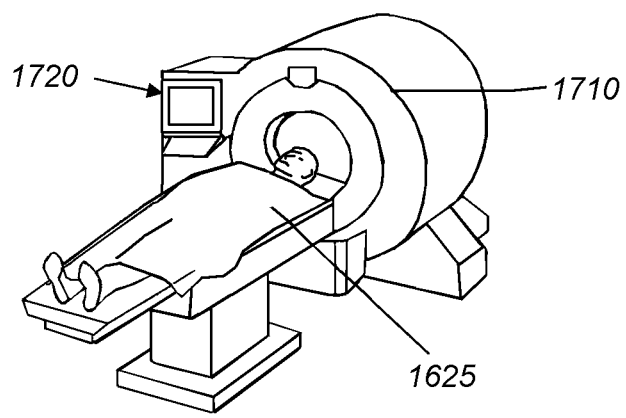
FIG. 17 is a perspective view of an imaging device and associated display used in imaging concentrations of nanoparticles in a patient, constructed and arranged according to the illustrative embodiment.

According to an illustrative embodiment, the nanoparticles of the nanoparticle agent injected in an exemplary patient 1625 are imaged using an image device having, for example, a drive field coil and a pickup device. As described generally herein, the patient undergoes any acceptable type or types of imaging to scan for the nanoparticles, for example, as shown in FIG. 17. Note, more particularly, that any imaging device can be employed capable of measuring the concentration of nanoparticles. The imaging device 1710 is constructed and arranged to detect the concentration of nanoparticles, as the nanoparticles are uptaken into the cancerous cells, and can be an MRI device, MPI device, or other arrangement to sense and detect nanoparticle spectroscopy. A display 1720 can be provided, which displays the concentration of nanoparticles, thereby imaging the cancer cells and allowing early detection of the cells. Laternatively, data can be directed to a storage device for subsequent display and/or analysis for concentrations of nanparticles and their particular localizations. This technique is shown by way of example in the case of ovarian cancer detection, due to its initial restriction to the peritoneal cavity, and thus nanoparticle injection can occur directly in the peritoneal cavity. Thus, the display 1720 will provide an image of the uptake, if any, of nanoparticles, thereby indicating the presence of cancer cells.

Again, note that is expressly contemplated that the term "image" and the term "imaging" can refer to a variety of information outputs and associated techniques for gathering useful information from infused nanoparticles that have been uptaken by cells (phagocytes) associated with malignant tumors. For example, in one form of basic imaging, spectroscopy is employed as an imaging technique to derive a general determination as to whether the concentration of nanoparticles has increased in a localized region. This is indicative of the presence of a malignancy, thereby providing a relatively inexpensive (when compared, for example to MRI imaging), technique for determining the presence of a malignant tumor in the body. After such a determination, further imaging can be undertaken (either contemporaneously or after a predetermined time interval) to determine the precise characteristics, size, shape, type, etc. of the timorous area/tissue. This further imaging can employ different and/or more-sensitive imaging devices than those initially employed on the localized areas of nanoparticles. These further imaging devices may or may not be particularly sensitive to nanoparticles. Such devices include, but are not limited to MRIs, etc. as described herein. The terms "image" and "imaging" are, therefore, expressly meant to include all types of external scanning mechanisms for localizing nanoparticles.

D. Diagnosis Using Nanoparticles

Figure 18:
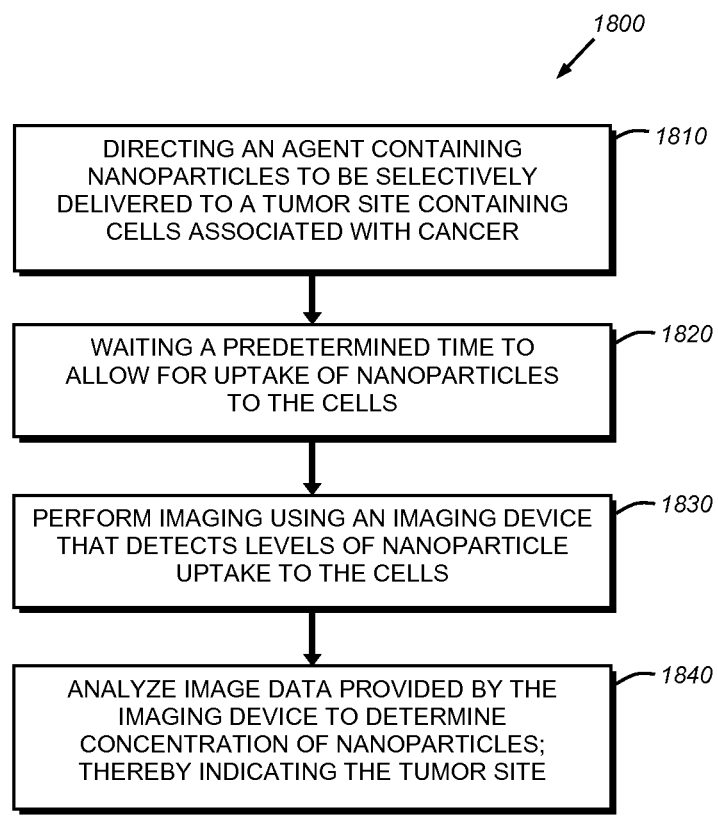
FIG. 18 is a flow diagram of a procedure for diagnosing certain cancers through nanoparticle-based agent injection and imaging, according to the illustrative embodiment.

Reference is now made to FIG. 18, showing an exemplary procedure 1800 for diagnosis of certain types of cancers, employing the nanotechnologies described herein. The procedure commences at step 1810 by directing an agent containing nanoparticles into a patient. The nanoparticles are selectively delivered proximate a cancer site containing cells associated with the cancer. This can be performed, for example, by directly administering a nanoparticle agent into a peritoneal cavity of a patient using a needle. Other techniques for administering the nanoparticle agent are apparent to those of ordinary skill. The concentration of nanoparticles administered in the agent is variable depending upon the sensitivity of the apparatus being employed, the treatment being performed, and other factors apparent to those of ordinary skill. In an illustrative embodiment, the total infusion of nanoparticles ranges from approximately 0.5 to 1.5 micrograms, and other levels of concentration within the body are expressly contemplated. As will be described below with reference to the clinical model, it has been determined that various cells are shown to selectively uptake the nanoparticles. The term "cancer cell(s)" as defined herein, refers to one or more cells residing in and around a tumor site. In a variety of tumors and cancer types, including the contemplated ovarian cancer model, it is recognized that these cells are expressed in tumor tissues and generally reside proximate the tumor. These cells are expressed in the tumors to allow for highlighting and imaging of the cancer cells through nanoparticle uptake. Notably, $CD11c^-$ human cells have been shown to most abundantly uptake the nanoparticles during a nanoparticle-based treatment. Likewise, CD45 cells, which are expressed as a result of tumorous tissue, also uptake nanoparticles. These cells collectively provide a high concentration of nanoparticles in regions that are proximate to a tumor mass.

After the nanoparticle agent has been administered, a predetermined time period lapses to allow for uptake of the nanoparticles to the cancer cells. Accordingly, at step 1820, a delay is provided for a predetermined time period to allow for uptake of nanoparticles to the cells. In an illustrative embodiment, the measurements of nanoparticle uptake would commence a few minutes (approximately 15 minutes, for example) following the injection, and continue for approximately an hour. There is a follow-up measurement that occurs between approximately 12 and 24 hours after injection to identify the regional collection of the nanoparticles. The predetermined time for waiting for nanoparticle uptake is highly variable depending upon the type of cancer and concentration of nanoparticles within the nanoparticle agent and can vary from minutes to hours to days. The first measurement taken after nanoparticle agent injection provides the activity of the immune system for a patient, and the later measurement provides the regions where the phagocytes collect the nanoparticles. A diagnosis would indicate that cancer is likely where the nanoparticles were uptaken quickly in the first measurement and collect in an ovary in the second measurement.

The phagocytes are drawn toward the cancer tissues, and have molecules called receptors on their surfaces that selectively uptake the nanoparticles for imaging purposes. Due to the tendency for phagocytes to be drawn toward inner solid tumors, their presence at the tumor site can be selectively targeted by the nanoparticles for uptake of the nanoparticles, useful in imaging and treatment of certain cancers. For example, detection of ovarian cancer can be accomplished by following the phagocytic cells in the peritoneum as they collect at the site of malignancy. The phagocytes are typically drawn deep within the tissue of the cancer or tumor and thus allow for early detection due to the uptake image as "highlighted" by the presence of elevated phagocytes now containing nanoparticles.

At procedure step 1830, imaging is performed using an imaging device that detects the uptake of nanoparticles into the cells. Any of the devices described herein can be employed for performing imaging of the nanoparticles, including MRI, MPI, optical imaging, and nanoparticle spectroscopy and other imaging devices and techniques apparent to those of ordinary skill. Finally, at step 1840, the image data provided by the imaging device is analyzed to determine the concentration of nanoparticles. This indicates whether cancer cells are present, depending upon the uptake of nanoparticles within the patient. Detection of nanoparticle uptake is used in diagnosing cancer cells and tumors.

E. Treatment Using Nanoparticles

Figure 19:
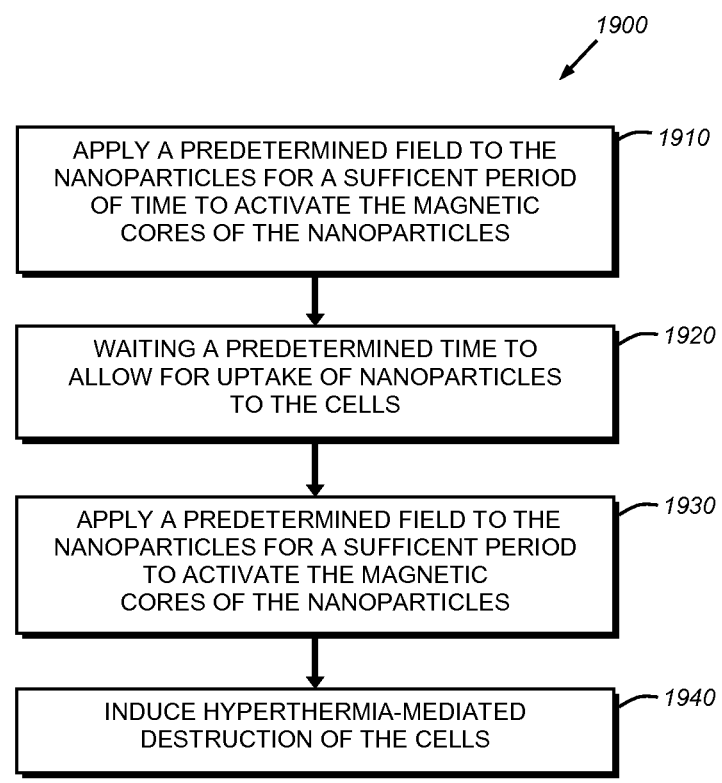
FIG. 19 is a flow diagram of a procedure for treating certain cancers through nanoparticle-based agent injection, according to the illustrative embodiment.

A nanoparticle-based agent administered as described herein can be further used in the treatment of cancer cells. As shown, for example, in the illustrative embodiment of FIG. 19, a procedure 1900 is disclosed for treatment of cancer cells. The procedure commences at step 1910 by directing an agent containing nanoparticles to be selectively delivered to a cancer site. The cancer site contains cells associated with a cancer, which selectively uptake the nanoparticles delivered in the agent. At step 1920, a predetermined time period is specified to allow for uptake of the nanoparticles into the cancer cells. This predetermined time period is highly variable depending upon the type of cancer treatment, the concentration of nanoparticles used, and the desired outcome of the treatment, and can range from minutes to hours or even days.

At step 1930, a field is applied to the nanoparticles for a sufficient period of time to activate the magnetic cores of the nanoparticles. This thereby induces hyperthermia-mediated destruction of the cells at step 1940, by heating up the nanoparticles, and more particularly the magnetic cores of the nanoparticles. The cancer cells are specifically targeted, as they uptake higher concentrations of the nanoparticles. Accordingly, the cancer cells that have taken up the nanoparticles can be destroyed by thereafter heating the nanoparticles.

F. Clinical Trials

Several clinical trials were performed in accordance with the above-described technologies employed for diagnosis and treatment of certain cancers, and particularly ovarian cancer. The results indicate that certain types of cancer cells do in fact uptake larger concentrations of nanoparticles, applicable in diagnosis and treatment of cancer cells and tumors. According to a clinical trial, two types of mice were tested to determine effect of nanoparticle uptake by certain types of cancer cells. The two types of mice include transgenic (Tg) mice and wild-type (WT) mice. The transgenic (Tg) mice concurrently carry a homozygous p53 gene (01XC2) plus an activated allele of K-ras (01XJ6) which is controlled by a Lox-Stop-Lox (LSL) cassette. The mouse strains 01XC2 and 01XJ6 are publicly available and more information is provided at http://web.ncifcrf.gov/researchresources/mmhcc/available_strains.asp. The wild-type mice are without the mutations. The mice were each injected with an adenovirus expressing Cre recombinase. The ovarian tumor size was then monitored for each type of mouse.

Figure 20:
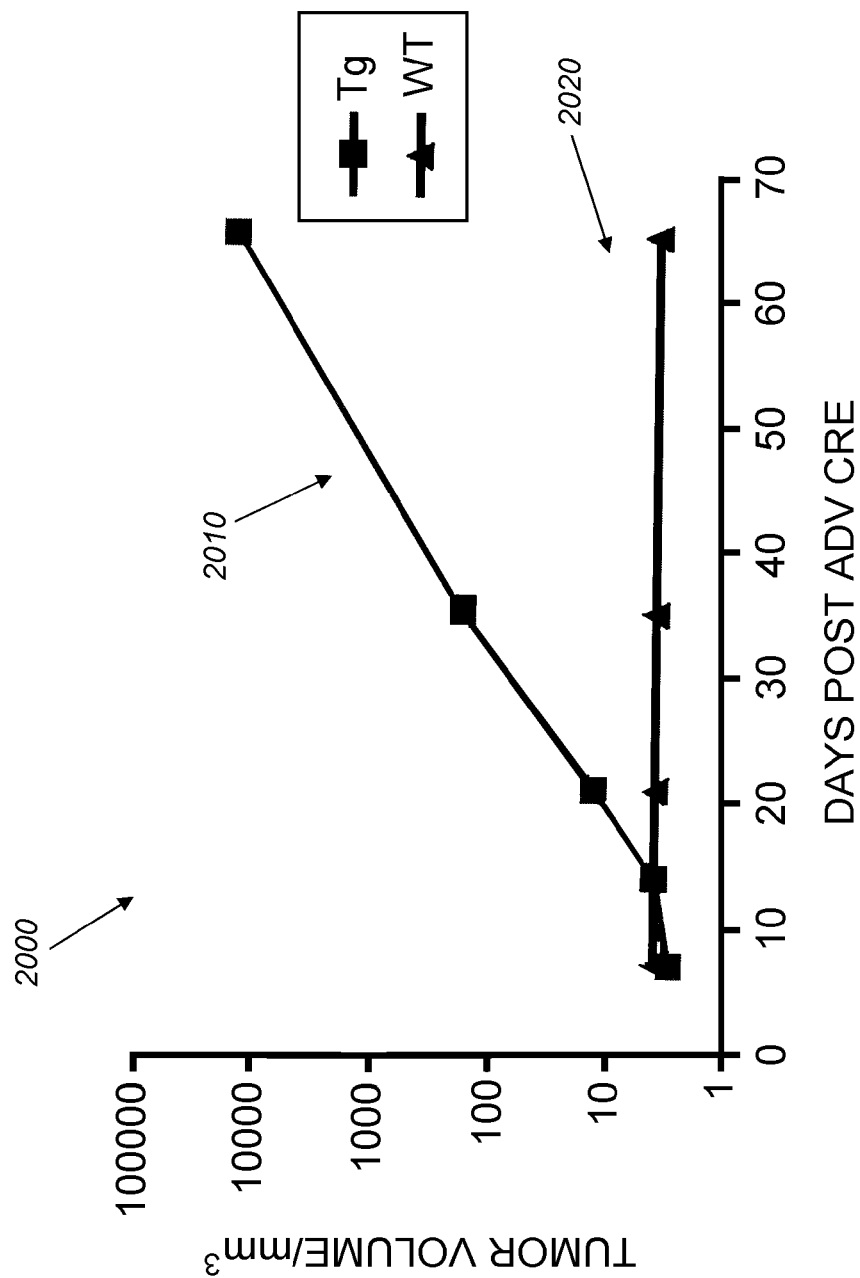
FIG. 20 is graph diagram showing tumor growth in transgenic and wild-type mice after being injected with adenovirus, according to a clinical model for use in proof of the illustrative procedure.

As shown in the graphical diagram 2000 of FIG. 20, the two types of mice exhibit substantially different volumes of the tumor post-injection. The transgenic (Tg) mouse, as indicated by line 2010, exhibits continued tumor growth as time progresses post administration of the adenovirus agent. Note the wild type (WT) mouse, as indicated by line 2020, does not experience increased tumor growth.

Figure 21:
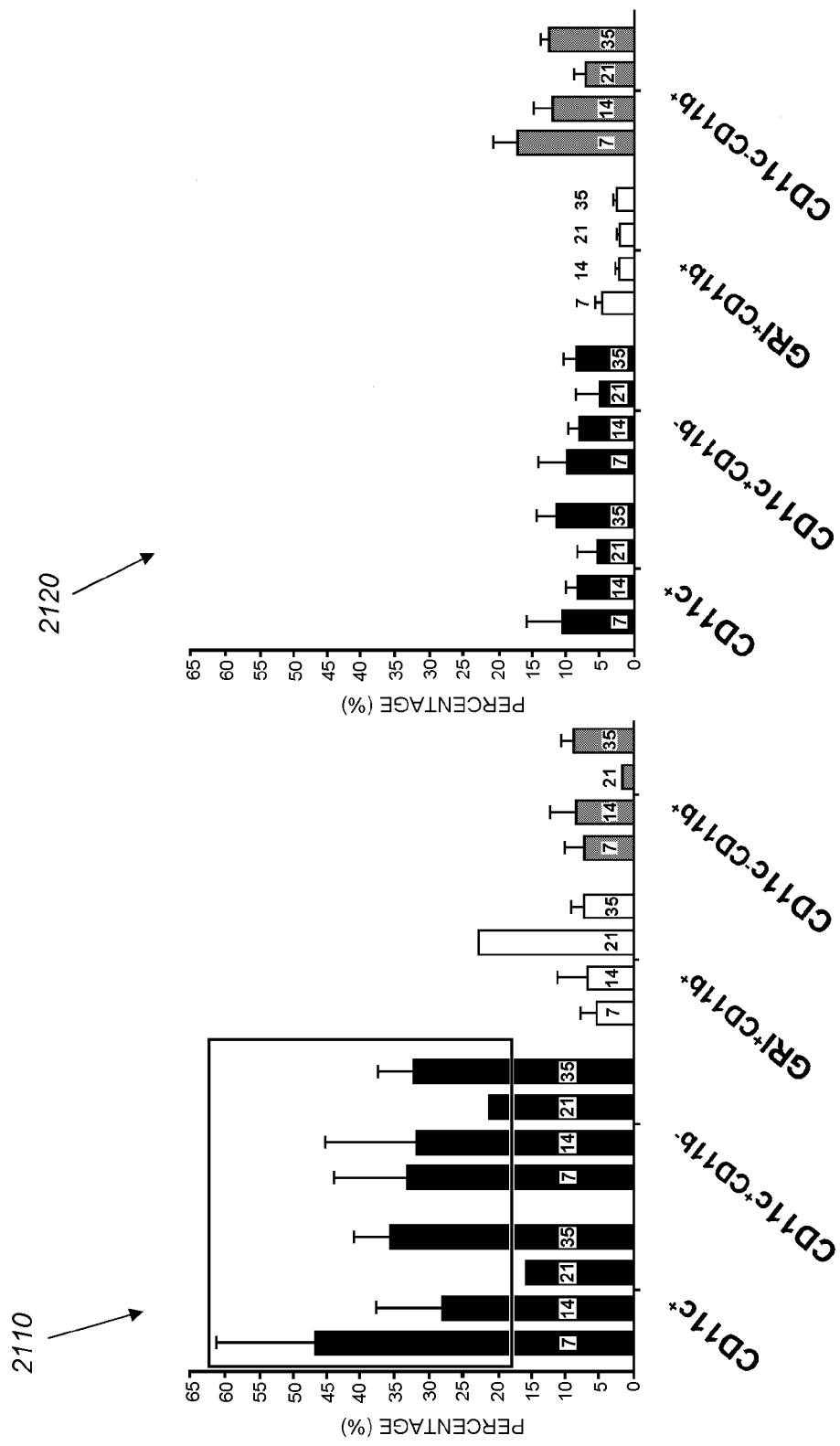
FIG. 21 is a graph diagram showing leukocyte uptake of nanoparticles in transgenic and wild-type mice, according to the clinical model.

The graphs 2110 and 2120 of FIG. 21 show, respectively, the uptake of nanoparticles at the transgenic (Tg) mouse and the wild type (WT) mouse. As shown in graph 2110, the $CD11c^+$ are the most abundant leukocytes at the site of ovarian tumors in the transgenic mice. This evidence shows that the leukocytes, particularly the $CD11c^+$ are abundant at tumor sites and thus can be selectively targeted by the nanoparticles in accordance with the techniques and devices described herein to accomplish diagnosis and treatment of certain cancers.

Figure 22:
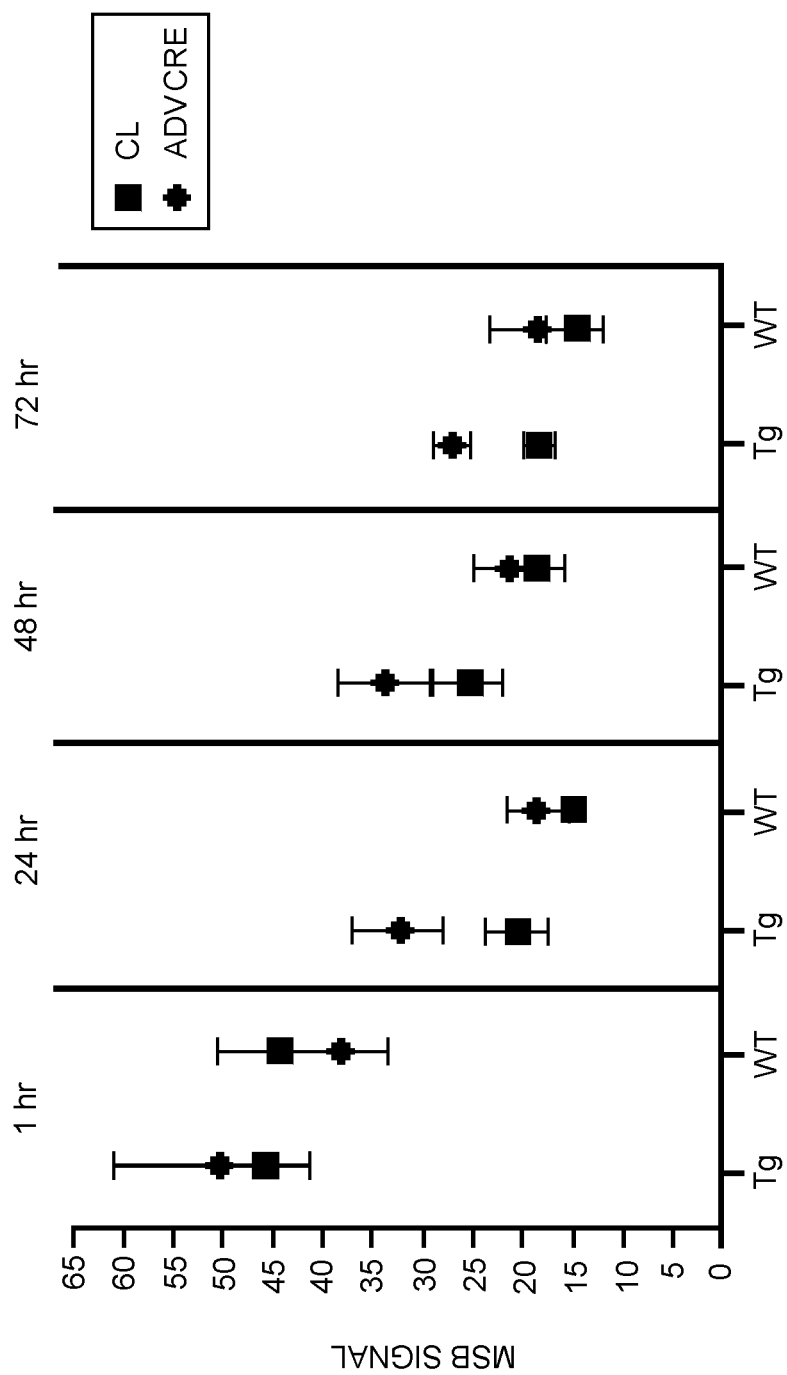
FIG. 22 is a graph diagram showing iron nanoparticle detection in transgenic and wild-type mice post injection, according to the clinical model.

Reference is now made to FIG. 22, showing a graph 2200 of the nanoparticle spectroscopy as detected using MSB signal technology for the transgenic mouse and the wild type mouse (note that this "imaging" technique can be employed to determine the general presence of a malignancy as described above). The separation of the signal does not occur in the wild type mice as with the transgenic mice. This indicates that there is a higher concentration of nanoparticles at the adenovirus injected cites than the contralateral (CL) sites. This further supports that indication of increased nanoparticles at the cancer cells.

It should be clear to those of ordinary skill that cancer detection and treatment can be accomplished using the devices and techniques described herein employ injection, detection and heating of nanoparticles. The results of the clinical trials indicate that concentrations of nanoparticles are greater at cancer cells and thus can be safely and effectively used in diagnosis and treatment of cancers. More particularly, leukocytes, and even more specifically $CD11c^+$, were found to most abundantly uptake the nanoparticles. Accordingly, the nanoparticles can selectively target the leukocytes to perform diagnosis and treatment of cancers.

As noted generally above, a basic application for the foregoing arrangements and procedures is for continuously measuring the temperature of the magnetic nanoparticles used to heat cancer cells in magnetic nanoparticle hyperthermia. A current limitation in the effective use of hyperthermia treatment is it is difficult to ascertain how hot the tissue becomes during heating. This difficulty arises in part due to blood flow and other physiological variables which modulate tissue cooling in unknown ways. Inserted temperature probes only measure temperature at one point. By measuring the spectrum of the nanoparticle magnetization, the temperature of the nanoparticles can be evaluated in real time. Using the imaging arrangement of FIG. 10, for example, in which the sensed temperature is coupled with an image of nanoparticle location, the resulting display image of the nanoparticles provides a visible a temperature map. Such a map can be displayed in grayscale or color in which differing colors and/or intensities represent differing temperature values within a desired range, and at predetermined locations.

Other factors such as the binding energies of the nanoparticles may complicate the overall reading of nanoparticles. However the above-described measurements may be adapted to compensate for secondary factors, thereby also providing estimates for those secondary factors. For example, it is contemplated that the principles described herein can be adapted to estimate the strength of the bonds of the antibody tag. Or the principles may be adapted to estimate the phase of the substrate in which the nanoparticles are imbedded/infused. Alternative, these principles may be adapted to estimate the mechanical rigidity of the cell or extracellular matrix to which a nanoparticle is attached. In general each of the above conditions would tend to modulate the motion of the nanoparticle at a given temperature, and thus would be reflected in $H_{TE}$. By empirical and experimental techniques, the effects of these factors can be plotted and coefficients (or curves, etc.) to characterize and/or detect these factors can be determined.

Measurements of the signal at different static bias fields, or with different amplitudes of the driving field, and/or with different combinations of frequencies of driving field all can be employed to provide information about the ability of the nanoparticles to tumble or reverse magnetic polarization. This information can be used to estimate various physical properties for the nanoparticle environment.

In a further illustrative embodiment of a cancer-treatment procedure, particles with antibodies targeted for cancer cells are injected in the subject. Following binding, a very large applied magnetic field is used to heat the particles in the cancer. The ratio of the harmonics would be used to monitor heating to make sure therapeutic temperatures are achieved in the cancer. In another embodiment, the distribution of the applied fields is changes using temperature information to achieve better therapy. In another embodiment, the harmonics at a constant temperature are used to measure the binding strength of the antibody targeting agents for diagnostic or other purposes including the suitability of therapy. In another embodiment, the harmonics at a constant temperature are used to estimate the number of antibody targeted particles that are bound and the number that are unbound for diagnostic purposes or to know when to start therapy. In another embodiment, the harmonics are used to estimate when a phase change has occurred in the material in which the articles are located.

IV. Superconducting Quantum Interference Device

Figure 23:
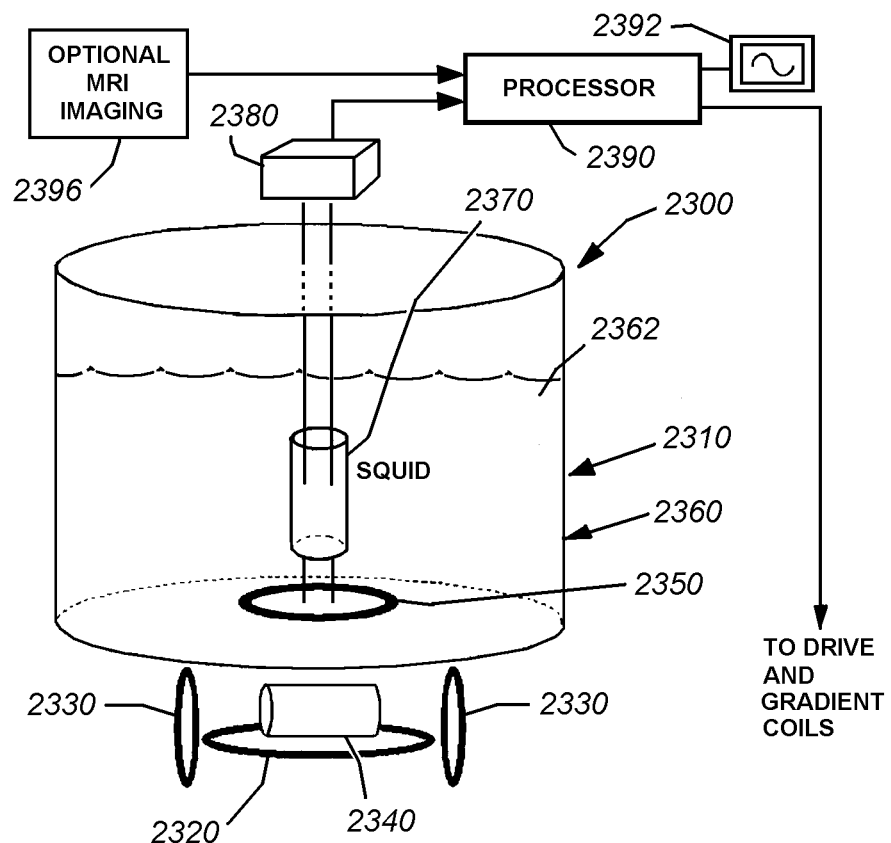
FIG. 23 is a magnetic nanoparticle detection/imaging system employing a very-high-sensitivity pickup device to measure the output signal from the magnetic nanoparticles in accordance with an illustrative embodiment.

Reference is now made to FIG. 23 which details an illustrative embodiment of an improvement to MPI device implementations, including the above-described sensing and localization embodiments, which significantly increases their sensitivity and imaging accuracy. This implementation can be used for a variety of applications including the particular cancer diagnosis and treatment system/method described in Section III above. By way of background, MPI typically imposes a pure sinusoidal magnetic field on the sample of embedded nanoparticles. Because no hysteresis curve is perfectly linear, the magnetization of the magnetic nanoparticles is distorted slightly, which produces harmonics in the induced magnetization. The induced magnetization produces a signal in the pickup coils, and that signal exhibits energy at the harmonics of the drive frequency. Those harmonics are unique to the nanoparticles and can be separated from the signal induced by the drive field because they are at different frequencies. Currently, the nanoparticle output signal is measured in a somewhat conventional pickup coil as described generally above.

The exemplary embodiment of an MPI system 2300, instead, employs a DC current or radio-frequency Superconducting Quantum Interference Device (SQUID) to increase the sensitivity of nanoparticle signal reception. The function of a SQUID, and its operation, is described in *The SQUID Handbook*, edited by John Clarke and Alex I. Braginski, Wiley-VCH, Weinheim, 2004, which is incorporated herein by reference as further background information. By using a SQUID the various harmonics in the above-described temperature sensing embodiment are better resolved, particularly for higher-order harmonics with correspondingly low signal outputs. In particular, conventional SQUID designs are capable of sensitivities on the order of $10^{-51}$ Tesla which is many orders of magnitude below that of a coil coupled to a traditional amplifier.

Further reference is now made to the exemplary MPI system 2300 of FIG. 23 MPI system which uses a SQUID detector assembly 2310 as a pickup device. Note that the illustrative drive coil 2320 and imaging gradient coils 2330 are similar, or identical to, those in previously described embodiments and/or the prior art. These coils 2320, 2330 surround a subject or sample 162340 infused with nanoparticles. The pickup coil 2350 resides over the sample 2340 and coils 2320, 2330, and is immersed in an insulated container (a cryostat) 2360 containing liquid helium 2362 to induce superconductivity (or the coil is otherwise held at a very low temperature using, for example cryogenic cooling jackets, etc.). The SQUID device 2370 is interconnected to the coil 2350 and is also immersed in the helium, or another low-temperature fluid 2362 to be maintained at a very low temperature. The system's sensing electronics 2380 interconnect to the SQUID and are located outside, adjacent to the cryostat 2360. The sensing electronics are part of, or interconnected to a data processor or other controller 2390 that also interconnects to the drive and gradient coils 2320, 2330 as shown. A display and interface 2392 provides image information and other data related to the sample 2340. The extremely high sensitivity of the SQUID device 2370 enables a very accurate image, and/or temperature (or other data) reading with respect to the sample 2340.

For optimal performance using the SQUID 2370 as a pickup device, the drive frequency generated by the drive coil 2320 should be prevented from dominating the output signal of the nanoparticles at higher harmonics. This can be accomplished in several ways. For example, the drive coil 2320 can be made resonant to the desired frequency, or a balancing coil can be placed at a location wherein it picks up the drive field but not the field output from the sample by the nanoparticles. Alternatively, the detector can be placed beside the drive coils with magnetic shielding between so the detector only observes the sample, and not the drive coil itself It is expressly contemplated that the SQUID device shown and described herein can be substituted for another form of "very-high-sensitivity pickup device" which can be employed in an illustrative imaging/sensing system in a generally similar position and manner. Thus, as used herein, that term should include other similar high-sensitivity devices, such as the recently developed Spin Exchange Relaxation-Free (SERF) magnetometer. A description of such a device can be found, by way of background, online in connection with the Princeton University Physics Department at the World Wide Web address: http/physics.princeton.edu/atomic/romalis/magnetometer/, the teachings of which are incorporated herein by reference by way of background.

It is also expressly contemplated that, according to this invention, a very-high-sensitivity pickup device can be applied as a detection system for any acceptable imaging system or method, or even to a system that is designed primarily to quantify the number of nanoparticles in a sample, without imaging the sample. Likewise, the SQUID or other high-sensitivity pickup can be incorporated into the imaging sensors described with reference to the above-described localization and imaging embodiments.

In accordance with this invention, the use of high-sensitivity pickups allows a variety of further subject characteristics to be measured. These characteristics include, but are not limited to, binding energies, bound fraction of nanoparticles, binding kinetics, phase changes in the materials containing the nanoparticles, and/or the stiffness of the elements the nanoparticles are bound to—such as extra-cellular matrix or cellular structures.

It is also contemplated generally that the MRI described above can be employed with any of the embodiments herein to measure particular characteristics, including binding and temperature, of particles. This is performed in the fringe field of the MRI, allowing the anatomical images produced by MRI to be co-registered with the particle images and measurements obtained using MPI techniques. The coregistration process can be accomplished using conventional image-handling techniques. As shown by way of example, in FIG. 10, the various localization and imaging embodiments can include such optional MRI imaging 1070, which is combined by the control and/or imaging components and software 1050 to produce a combined/coregistered image on the display 1060. Likewise, various temperature and other particle-characteristic sense embodiments can be combined with MRI imaging as depicted by way of example in FIG. 23. As shown the optional MRI imaging has acquired anatomical (or other) images of the subject 2340, which are then combined/coregistered with particle imaging using the controller components and software 2390 to generate the combined image on the display 2392.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. In particular, it is contemplated that in most embodiments coils are arranged to generate fields that act in three dimensions, although one dimension of action may be shown for simplicity. The selection and arrangement of magnetic coils (or other selectively driven magnetic structures) should be apparent to those of ordinary skill. Moreover, the magnetic fields-as-functions-of-time employed herein can include, but are not limited, to linear and nonlinear magnetic field gradients, harmonic fields with different frequencies, different phases and different field orientations and fields that are arbitrary functions of time. The magnetic fields can vary with position with equal generality. Notably, many types of cancers can be diagnosed and treated using the nanoparticle imaging and heating technologies described hereinabove. All of the above-described embodiments can be employed as discrete systems and methods or combined with MPI methods or the imaging methods described here or other imaging methods to create images of the parameters measured. For example, by combining a plurality of systems and methods temperature maps or temperature images can be obtained instead of determining the average temperature in a single volume. In addition, while control systems are shown schematically, it should be apparent to those of ordinary skill that any acceptable arrangement of analog and/or digital electronic hardware, software (consisting of computer readable program instructions in association with a processor) or a combination of hardware and software can be employed to achieve the desired control, localization and other desired sensing and display functions. Also, while the exemplary experimental arrangement shown and described herein for the sensing of temperature is adapted for use on small samples, the scale of the arrangement can be altered in accordance with well-known design techniques to accommodate larger samples and subjects including human bodies. Likewise, a variety of additional scanning and measurement devices can be employed in accordance with ordinary skill to provide additional useful metrology. Accordingly, this description is meant to be taken only by way of example, and not to otherwise limit the scope of this invention.

What is claimed is:

1. A magnetic particle imaging (MPI) method of diagnosing certain cancers in which phagocytes selectively uptake iron-based nanoparticles, the MPI method comprising the steps of:
   directing a compound containing the iron-based nanoparticles to be selectively delivered via phagocyte uptake to a tumor site containing cells;
   allowing a predetermined time for the iron-based nanoparticles to be uptaken into the cells contained at the tumor site;
   performing magnetic particle imaging using a magnetic particle imaging device in order to detect a concentration of iron-based nanoparticles uptaken into the cells;
   analyzing image data provided by the magnetic particle imaging device in order to determine the concentration of iron-based nanoparticles indicative of the tumor site; and
   applying a predetermined magnetic field to the iron-based nanoparticles for a sufficient period in order to activate a magnetic core of the iron-based nanoparticles, thereby inducing hyperthermia destruction of the cells.

2. The MPI method as set forth in claim 1 wherein the tumor site is ovarian cancer and the directing of the compound containing the iron-based nanoparticles is delivered into a peritoneal cavity.

3. The MPI method as set forth in claim 1 wherein the magnetic particle imaging device also comprises a magnetic resonance imaging (MRI) device.

4. The MPI method as set forth in claim 1 wherein the magnetic particle imaging device comprises a drive field coil and a pickup mechanism.

5. The MPI method as set forth in claim 1, wherein allowing a predetermined time further comprises:
   conducting a first measurement of the compound, at a first time indicative of an activity level of an immune system of a subject; and
   conducting a second measurement of the compound, at a second time, the second time being later than the first time, and indicative of at least one region of the phagocyte uptake.

6. The MPI method as set forth in claim 1 wherein the iron-based nanoparticles are iron oxide nanoparticles.

7. The MPI method as set forth in claim 1 wherein the magnetic particle imaging device comprises:
   drive and selection coils that generate a magnetic field which provides a sub-saturation region within a subject containing iron-based nanoparticles;
   sensors that read signals from the iron-based nanoparticles adjacent to the sub-saturation region; and
   supplemental coils that provide at least one of a static magnetic field offset and a gradient magnetic field so as to improve the localization characteristics of the signals whereby the magnetic particle imaging is improved.

8. The MPI method as set forth in claim 1 wherein the magnetic particle imaging device comprises:
   a pair of drive coils that each generate a magnetic field which provides a sub-saturation region within a subject containing iron-based nanoparticles;
   a control system that generates magnetic fields having each of two discrete frequencies in each of the pair of drive coils;
   sensors that read signals from the iron-based nanoparticles adjacent to the sub-saturation region; and
   a magnetic particle imaging system, operatively connected to the sensors and the control system, that localizes the nanoparticles based on the signals in response to information derived from the two discrete frequencies.

9. The MPI method as set forth in claim 8 wherein the magnetic particle imaging device further comprises an MRI constructed and arranged to derive an MRI image of the subject and wherein the combined magnetic particle and magnetic resonance imaging system is constructed and arranged to co-register an image of the MPI along with an the MRI image.

10. The MPI method as set forth in claim 1 further comprising providing an MRI that derives an MRI image of the subject and an image of the MPI along with an MRI image.

11. The MPI method as set forth in claim 1 wherein the magnetic particle imaging device comprises a spectroscopy device that determines the concentration of the iron-based nanoparticles.

12. The MPI method as set forth in claim 11 further comprising performing a further imaging of an area in which the concentration of the iron-based nanoparticles is localized in order to determine predetermined features of the tumor site.

13. The MPI method as set forth in claim 1 wherein the further imaging is performed using an MRI that is constructed and arranged in order to detect the iron-based nanoparticles.

14. A Magnetic Particle imaging(MPI) system configured for diagnosing certain cancers in which phagocytes selectively uptake iron-based nanoparticles comprising:
   a compound containing the iron-based nanoparticles that is selectively delivered via phagocyte uptake to a tumor site containing cells; and
   a magnetic particle imaging device that, a predetermined time after the iron-based nanoparticles are delivered, detects a concentration of the iron-based nanoparticles uptaken into the cells, and provides magnetic particle image data that allows a determination of the concentration of iron-based nanoparticles indicative of the tumor site; wherein the magnetic particle imaging device comprises:
      drive and selection coils that generate a magnetic field which provides a sub-saturation region within a subject containing iron-based nanoparticles;
      sensors that read signals from the iron-based nanoparticles adjacent to the sub-saturation region; and
      supplemental coils that provide at least one of a static magnetic field offset and a gradient magnetic field so as to improve the localization characteristics of the signals whereby the magnetic particle imaging is improved.

15. The MPI system as set forth in claim 14 wherein the tumor site is at a peritoneal cavity that is being used for treating ovarian cancer.

16. The MPI system as set forth in claim 14 wherein the magnetic particle imaging device also comprises a magnetic resonance imaging (MRI) device.

17. The MPI system as set forth in claim 14 wherein the iron-based nanoparticles are iron oxide nanoparticles.

18. A Magnetic Particle Imaging (MPI) system configured for diagnosing certain cancers in which phagocytes selectively uptake iron-based nanoparticles comprising:
   a compound containing the iron-based nanoparticles that is selectively delivered via phagocyte uptake to a tumor site containing cells; and
   a magnetic particle imaging device that, a predetermined time after the iron-based nanoparticles are delivered, detects a concentration of the iron-based nanoparticles uptaken into the cells, and that provides image data that allows a determination of the concentration of the iron-based nanoparticles indicative of the tumor site;
   wherein the magnetic particle imaging device comprises:
      a pair of drive coils that each generate a magnetic field which provides a sub-saturation region within a subject containing the iron-based nanoparticles;
      a control system that generates magnetic fields having each of two discrete frequencies in each of the pair of drive coils;
      sensors that read signals from the iron-based nanoparticles adjacent to the sub-saturation region; and
      a magnetic particle imaging system, operatively connected to the sensors and the control system, that localizes the iron-based nanoparticles based on the signals in response to information derived from the two discrete frequencies.

19. The MPI system as set forth in claim 18 wherein the magnetic particle imaging device further comprises an MRI constructed and arranged to derive an MRI image of the subject and wherein the combined magnetic particle and magnetic resonance imaging system is constructed and arranged to co-register an image of the MPI along with the MRI image.

20. The MPI system as set forth in claim 18 wherein the tumor site is at a peritoneal cavity that is being used for treating ovarian cancer.

* * * * *